US009597297B2

(12) United States Patent
Cohen et al.

(10) Patent No.: US 9,597,297 B2
(45) Date of Patent: *Mar. 21, 2017

(54) COMBINATION OF PILOCARPIN AND METHIMAZOL FOR TREATING CHARCOT-MARIETOOTH DISEASE AND RELATED DISORDERS

(71) Applicant: PHARNEXT, Issy les Moulineaux (FR)

(72) Inventors: Daniel Cohen, Le Vesinet (FR); Ilya Chumakov, Vaux-le Penil (FR); Serguei Nabirochkin, Chatenay Malabry (FR); Oxana Guerassimenko, Milly-la-Foret (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,783

(22) Filed: May 5, 2014

(65) Prior Publication Data

US 2014/0235599 A1   Aug. 21, 2014

Related U.S. Application Data

(63) Continuation of application No. 12/999,125, filed as application No. PCT/EP2009/057544 on Jun. 17, 2009, now Pat. No. 8,716,269.

(30) Foreign Application Priority Data

Jun. 18, 2008 (EP) .................................... 08305280

(51) Int. Cl.

| A61K 31/56 | (2006.01) |
| A61K 31/4164 | (2006.01) |
| A61P 25/00 | (2006.01) |
| A61K 31/4178 | (2006.01) |
| A61K 31/047 | (2006.01) |
| A61K 31/197 | (2006.01) |
| A61K 45/06 | (2006.01) |
| A61K 31/192 | (2006.01) |
| A61K 31/436 | (2006.01) |
| A61K 31/439 | (2006.01) |
| A61K 31/485 | (2006.01) |
| A61K 31/575 | (2006.01) |

(52) U.S. Cl.
CPC .......... *A61K 31/047* (2013.01); *A61K 31/192* (2013.01); *A61K 31/197* (2013.01); *A61K 31/4164* (2013.01); *A61K 31/4178* (2013.01); *A61K 31/436* (2013.01); *A61K 31/439* (2013.01); *A61K 31/485* (2013.01); *A61K 31/575* (2013.01); *A61K 45/06* (2013.01)

(58) Field of Classification Search
USPC ....................... 514/171, 397, 392
See application file for complete search history.

(56) References Cited

U.S. PATENT DOCUMENTS

| 6,391,922 B1 | 5/2002 | Fogel |
| 8,741,886 B2 | 6/2014 | Cohen et al. |
| 2001/0004640 A1 | 6/2001 | Inada et al. |
| 2001/0023246 A1 | 9/2001 | Barritault et al. |
| 2003/0069213 A1 | 4/2003 | Il et al. |
| 2004/0102525 A1 | 5/2004 | Kozachuk |
| 2005/0187290 A1 | 8/2005 | Fontes et al. |
| 2007/0099947 A1 | 5/2007 | Dean, III et al. |
| 2008/0188510 A1 | 8/2008 | Yoshino |
| 2009/0069419 A1 | 3/2009 | Jandeleit et al. |
| 2009/0197958 A1 | 8/2009 | Sastry et al. |
| 2010/0029654 A1 | 2/2010 | Pasinetti |
| 2010/0310641 A1 | 12/2010 | Cohen et al. |
| 2011/0230659 A1 | 9/2011 | Tsukamoto et al. |
| 2012/0040940 A1 | 2/2012 | Cohen et al. |
| 2012/0058992 A1 | 3/2012 | Cohen et al. |
| 2012/0088744 A1 | 4/2012 | Cohen et al. |
| 2012/0270836 A1 | 10/2012 | Cohen et al. |
| 2013/0085122 A1 | 4/2013 | Cohen et al. |
| 2013/0090307 A1 | 4/2013 | Cohen et al. |
| 2014/0178413 A1 | 6/2014 | Tang et al. |

FOREIGN PATENT DOCUMENTS

| EP | 0778023 | 6/1997 |
| EP | 1 563 846 | 8/2005 |
| EP | 1 837 034 | 9/2007 |
| EP | 2065038 | 6/2009 |
| WO | WO 00/20024 | 4/2000 |
| WO | WO 01/58476 | 8/2001 |
| WO | WO 03/007993 | 1/2003 |
| WO | WO 03/080068 | 10/2003 |
| WO | WO 2004/006911 | 1/2004 |

(Continued)

OTHER PUBLICATIONS

Akan, P. et al. "Pregnenolone protects the PC-12 cell line against amyloid beta peptide toxicity but its sulfate ester does not" *Chemico-Biological Interactions*, 2009, pp. 65-70, vol. 177, No. 1, XP-002613421.

Andrieu, S. et al. "Association of Alzheimer's Disease Onset With Ginkgo Biloba and Other Symptomatic Cognitive Treatments in a Population of Women Aged 75 Years and Older From the EPIDOS Study" *Journal of Gerontology: Medical Sciences*, Apr. 2003, pp. 372-377, vol. 58A, No. 4, XP-009144763.

Aplin, A. C. et al. "Vascular regression and survival are differentially regulated by MT1-MMP and TIMPs in the aortic ring model of angiogenesis" *Am. J. Physiol Cell Physiol*, Aug. 2009, pp. C471-C480, vol. 297, No. 2, XP-002613424.

(Continued)

*Primary Examiner* — Kathrien Cruz
(74) *Attorney, Agent, or Firm* — Saliwanchik, Lloyd & Eisenschenk

(57) ABSTRACT

The present invention relates to compositions and methods for the treatment of the Charcot-Marie-Tooth disease and related peripheral neuropathies. More particularly, the invention relates to combined therapies for treating said disease by affecting simultaneously muscarinic receptor signalling and thyroid hormone pathway in a subject.

9 Claims, 6 Drawing Sheets

(56) References Cited

FOREIGN PATENT DOCUMENTS

Figure 1:
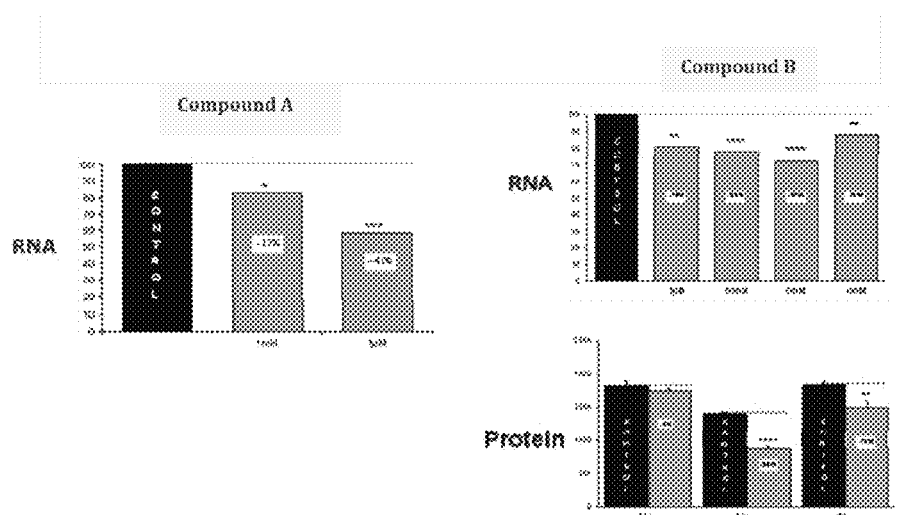

| WO | WO 2004/019938 | 3/2004 |
|---|---|---|
| WO | WO 2006/117573 | 11/2006 |
| WO | WO 2007/053596 | 5/2007 |
| WO | WO 2008/006070 | 1/2008 |
| WO | WO 2008/143361 | 11/2008 |
| WO | WO 2009/068668 | 6/2009 |
| WO | WO 2009/133128 | 11/2009 |
| WO | WO 2009/133141 | 11/2009 |
| WO | WO 2009/133142 | 11/2009 |
| WO | WO 2009/153291 | 12/2009 |
| WO | WO 2010/061931 | 6/2010 |
| WO | WO 2010/139627 | 12/2010 |
| WO | WO 2011/054759 | 5/2011 |
| WO | WO 2012/117076 | 9/2012 |

OTHER PUBLICATIONS

Dobrek, L. et al. "Future Potential Indications for Pharmacotherapy Using Renin-Angiotensin-Aldosterone System Inhibitory Agents" *Adv. Clin. Exp. Med.*, May 2010, pp. 389-398, vol. 19, No. 3, XP-009144580.

Finsterer, J. et al. "Neurotoxocarosis" *Rev. Inst. Med. Trop. S. Paulo*, pp. 279-287, Sep.-Oct. 2007, vol. 49, No. 5, XP-002623261.

Kakinuma, Y. et al. "Donepezil, an acetylcholinesterase inhibitor against Alzheimer's dementia, promotes angiogenesis in an ischemic hindlimb model" *Journal of Molecular and Cellular Cardiology*, Apr. 2010, pp. 680-693, vol. 48, No. 4, XP-26949580.

Klein, H.E. et al. "Calcium antagonists in dementias. Assessment of the therapeutic efficacy" *Munchener Medizinische Wochenschrift*, 1995, pp. 38, 41-43, vol. 137, No. 47, XP-001525484.

Lee, S.T. et al. "Reduced circulating angiogenic cells in Alzheimer disease" *Neurology*, May 1, 2009, pp. 1858-1863, vol. 72, No. 21, XP-002610857.

Lu, Y. et al. "Neuroprotective activity and evaluation of Hsp90 inhibitors in an immortalized neuronal cell line" *Bioorganic & Medicinal Chemistry*, Feb. 2009, pp. 1709-1715, vol. 17, No. 4, XP-002613422.

Parnetti, L. et al. "Vascular Dementia Italian Sulodexide Study (VA.D.I.S.S.) Clinical and Biological Results" *Thrombosis Research*, pp. 225-233, vol. 87, No. 2.

Polizopoulou, Z. S. et al. "Evaluation of a Proposed Therapeutic Protocol in 12 Dogs with Tentative Degenerative Myelopathy" *Act Veterinaria Hungarica*, pp. 293-301, Sep. 2008, vol. 56, No. 3, XP-009142152.

Roehl, A. B. et al. "Neuroprotective properties of levosimendan in an in vitro model of traumatic brain injury" *BMC Neurology*, Oct. 21, 2010, pp. 1-4, vol. 10, No. 1, XP-021074880.

Spuch, C. et al. "Induction of angiogenesis by implantation of encapsulated cells expressing vegf: A new therapy approach on Alzheimer's disease?" *Journal of Neurological Sciences*, Aug. 2009, p. 260, vol. 283, No. 1-2, Issue 1, XP-002571001.

Van Den Bussche, H. et al. "Prescription patterns and effectiveness perception of anti-dementia drugs—A comparison between General Practitioners, Neurologists and Psychiatrists" *Nervenheilkunde*, 2005, pp. 485-492, vol. 24, No. 6, XP-009144765.

Wang, B. et al. "Protective Effects of Wu-Zi-Yan-Zong-Fang on Amyloid β-induced Damage In Vivo and In Vitro" *Database Biosis [Online] Biosciences Information Service*, Aug. 2009, pp. 941-948, vol. 129, No. 8.

Yoshida, K. et al. "Eplerenone Enhances Neovascularization Induced by Endothelial Progenitor Cells in Rat Hindlimb Ischemia" *18th Scientific Meeting of the European-Society-of-Hypertension, 22nd Scientific Meeting of the Inter*, Berlin, Germany, Jun. 14-19, 2008, Poster session PJ-413, XP-009144604, abstract only.

Database Biosis [Online] Bioscience Information Service, Philadelphia, PA, Yoshihiko, K. et al. "Donepezil, an acetylcholiesterase inhibitor against Alzheimer's dementia, promotes angiogenesis in an ischemic limb model of nicotinic alpha 7 k0 mice" Database Accession No. PREV200800197710, Oct. 2007, pp. 1-2, vol. 116, No. 16, Suppl. S., XP-002613420.

Database Biosis [Online] Bioscience Information Service, Philadelphia, PA, Wang, B. et al. "Protective Effects of Wu-Zi-Yan-Zong-Fang on Amyloid β-induced Damage In Vivo and In Vitro" Database Accession No. PREV200900521928, Aug. 2009, pp. 1-2, vol. 129, No. 8, Suppl. S., XP-002613423.

Hama, A. et al. "Synergistic interaction between intrathecal gamma-aminobutyrate (GABA) receptor agonists and an N-methyl-D-aspartate (NMDA) receptor antagonist in rats with neuropathic spinal cord injury pain" *Society for Neuroscience Abstract Viewer and in Itinerary Planner*, 2010, p. 1, vol. 40.

Lyden, P.D. et al. "Combination therapy protects ischemic brain in rats. A glutamate antagonist plus a gamma-aminobutyric acid agonist" *Stroke*, 1994, pp. 189-196, vol. 25.

Costa, C. et al. "Coactivation of $GABA_A$ and $GABA_B$ Receptor Results in Neuroprotection During in Vitro Ischemia" *Stroke*, Jan. 15, 2004, pp. 596-600, vol. 35.

Zhou, C. et al. "Neuroprotection of γ-Aminobutyric Acid Receptor Agonists Via Enhancing Neuronal Nitric Oxide Synthase (Ser847) Phosphorylation Through Increased neuronal Nitric Oxide Synthase and PSD95 Interaction and Inhibited Protein Phosphatase Activity in Cerebral Ischemia" *Journal of Neuroscience Research*, 2008, pp. 2973-2983, vol. 86.

Louzada, P. R. et al. "Taurine prevents the neurotoxicity of β-amyloid and glutamate receptor agonists: activation of GABA receptors and possible implications for Alzheimer's disease and other neurological disorders" *The FASEB Journal*, Mar. 2004, vol. 18.

Engelhard, K. et al. "Der neuroprotektive Einfluss des Glutamat-Antagonisten Acamprosat nach experimenteller zerebraler Ischämie" *Der Anaesthesist*, Sep. 22, 2000, pp. 816, 818, and 820, vol. 49, No. 9.

Slavik, J. et al. "In Vitro Correlates of in Vivo Rapamycin Therapy in Patients with Multiple Sclerosis" *Clinical Immunology*, Jan. 1, 2006, p. S113, vol. 119.

Pomara, N. et al. "Mifepristone (RU 486) for Alzheimer's disease" *Neurology*, May 1, 2002, p. 1436, vol. 58, No. 9.

Gallagher, P. et al. "Persistent effects of mifepristone (RU-486) on cortisol levels in bipolar disorder and schizophrenia" *Journal of Psychiatric Research*, Oct. 1, 2008, pp. 1037-1041 vol. 42, No. 12.

Zu Horste, G. M. et al. "Myelin disorders: Causes and Perspectives of Charcot-Marie-Tooth Neuropathy" *Journal of Molecular Neuroscience*, Jan. 1, 2006, pp. 77-88, vol. 28, No. 1.

Herrmann, D. N. et al. "Experimental Therapeutics in Hereditary Neuropathies: The Past, the Present and the Future" *Neurotherapeutics*, Jan. 1, 2008, pp. 507-515, vol. 5, No. 4.

Gironi, M. et al. "A pilot trial of low-dose naltrexone in primary progressive multiple sclerosis" *Multiple Sclerosis*, Sep. 1, 2008, pp. 1076-1083, vol. 14, No. 8.

Cintas, P. et al. "Drug therapy for symptomatic relief in ALS-Quels sont les traitements medicamenteux syptomatiques?" *Revue Neurologique*, Jun. 1, 2006, pp. 4S235-4S243, vol. 162.

Norris, F. H. et al. "Trial of Baclofen in Amyotrophic Lateral Sclerosis" *Archives of Neurology*, Nov. 1, 1979, pp. 715-716, vol. 36.

Lees, A. J. et al. "Baclofen in Parkinson's disease" *Journal of Neurology, Neurosurgery & Psychiatry*, Jan. 1, 1978, pp. 707-708, vol. 41.

Chemidex Pharma Ltd. "Lyflex 5mg/5ml Oral Solution" XP-002476376, retrieved from the internet: http://emc.medicines.org.uk/emc/assets/c/html/DisplayDoc.asp?document ID=14939, Apr. 14, 2008.

Wilcock, G. K. et al. "A placebo-controlled, double-blind trial of the selective AB-42 lowering agent, flurizan (MPC-7869, (R)-flurbiprofen) in patients with mild to moderate Alzheimer's disease" *Alzheimer's & Dementia: The Journal of the Alzheimer's Association*, Jul. 1, 2005, p. S95, vol. 1, No. 1, Abstract O2-01-05.

Keltner, J. L. "Myotonic Pupils in Charcot-Marie-Tooth Disease, Successful Relief of Symptoms with 0.025% Pilocarpine" *Achieves of Ophthalmology*, Jan. 1, 1975, pp. 1141-1148, vol. 93, No. 11.

Written Opinion in International Application No. PCT/EP2010/057438, Nov. 4, 2010, pp. 1-11.

(56) References Cited

OTHER PUBLICATIONS

Berenbaum, M.C., "Synergy, additivism and antagonism in immunosuppression: A Critical Review," *Clin. exp. Immunol.*,1977, pp. 1-18, vol. 28.

Jalbert, J.J. et al., "Dementia of the Alzheimer Type," *Epidemiologic Reviews*, 2008, pp. 15-34, vol. 30.

Jantzen and Robinson, *Modern Pharaceutics 3rd Edition*, published 1996, Marcel Dekker Inc., New York, NY, ed. Gilbert S. Banker et al., p. 596.

Levin, E.D. et al., "Baclofen interactions with nicotine in rats: effects on memory," *Pharmacology, Biochemistry and Behavior*, 2004, pp. 343-348, vol. 79.

Rogers, S.L. et al., "Donepezil Improves Cognition and Global Function in Alzheimer Disease," *Arch Intern Med*, 1998, pp. 1021-1031, vol. 158.

Rosse, R.B. et al., "Baclofen Treatment in a Patient With Tardive Dystonia," *J. Clin Psychiatry*, 1986, pp. 474-475, vol. 47.

Wilcox, D.M. et al., "Anti-Aβ immunotherapy in Alzheimer's disease; relevance of transgenic mouse studies to clinical trials," *J. Alzheimers Dis.*, 2008, pp. 555-569, vol. 15, No. 4.

Flannery, B. A. et al., "Baclofen for Alcohol Dependence: A Preliminary Open-Label Study", *Alcoholism Clinical and Experimental Research*, 2004, pp. 1517-1523, vol. 28, No. 10.

Soyka, M., "Efficacy of acamprostate in the relapse of alcohol dependence. Results of clinical trials and therapeutical prospects," *Nervenhelikunde*, 1995, pp. 83-86, vol. 14, No. 2, Abstract.

Colombo, G. etal., "Role of GABA (B) receptor in alcohol dependence: reducing effect of baclofen on alcohol intake and alcohol motivational properties in rats and amelioration of alcohol withdrawal syndrome and alcohol craving in human alcoholics," *Neurotoxicity research*, 2004, pp. 403-414, vol. 6, No. 5, Abstract.

Binbay, Z. et al., "The efficacy of donepezil in two cases with alcohol induced Korsakoff's syndrome," *Klinik Pasikofarmakoloji Bulteni*, 2008, pp. 46-49, vol. 18, No. 1, Abstract.

Lu, P. et al., "Silibinin prevents amyloid β peptide-induced memory impairment and oxidative stress in mice," *British Journal of Pharmacology*, 2009, pp. 1270-1277, vol. 157.

Zemljic, G. et al., "Levosimendan Improves Renal Function in Patients With Advanced Chronic Heart Failure Awaiting Cardiac Transplantation," *Journal of Cardiac Failure*, 2007, pp. 417-421, vol. 13, No. 6.

Saba, H. I. et al., "Brief Report: Treatment of Bleeding in Hereditary Hemorrhagic Telangiectasia With Aminocaproic Acid," *New Engl. J. Med*, 1994, pp. 1789-1790, vol. 330.

Pooler, A. M. et al. "The 3-hydroxy-3-methylglutaryl co-enzyme A reductase inhibitor pravastatin enhances neurite outgrowth in hippocampal neurons" *Journal of Neurochemistry*, May 2006, pp. 716-723, vol. 97, No. 3, XP-002571001.

Brasser, S. M. et al. "Alcohol Effects During Acamprosate Treatment: A Dose-Response Study in Humans" *Alcoholism: Clinical and Experimental Research*, Jul. 2004, pp. 1074-1083, vol. 28, No. 7.

Froestl, W. et al. "SGS742: the first $GABA_B$ receptor antagonist in clinical trials" *Biochemical Pharmacology*, 2004, pp. 1479-1487, vol. 68.

Izquierdo, I. et al. "Correlation between the Pharmacology and Long-Term Potentiation and the Pharmacology of Memory" *Neurobiology of Learning and Memory*, 1995, pp. 19-32, vol. 63.

Lipton, S. "Failures and Successes of NMDA Receptor Antagonists: Molecular Basis for the Use of Open-Channel Blockers like Memantine in the Treatment of Acute and Chronic Neurologic Insults" *NeuroRx: The Journal of the American Society for Experimental NeuroTherapeutics*, Jan. 2004, pp. 101-110, vol. 1.

Nakagawa, Y. et al. "The $GABA_B$ receptor antagonist CGP36742 attenuates the baclofen- and scopolamine-induced deficit in Morris water maze task in rats" *Brain Research*, 1997, pp. 101-106, vol. 766.

Tang, A. et al. "Effect of long term baclofen treatment on recognition memory and novelty detection" *Behavioural Brain Research*, 1996, pp. 145-152, vol. 74.

Van Der Staay, F. J. et al. "Effects of the cognition impairer MK-801 on learning and memory in mice and rats" *Behavioural Brain Research*, 2011, pp. 215-229, vol. 220.

Bassi, S. et al. "Encephalomyelitis with Thyrotoxicosis," *Journal of Neurology*, 1978, pp. 293-296, vol. 218.

Coffey, R. J. et al. "Familial Trigeminal Neuralgia and Charcot-Marie-Tooth Neuropathy Report of Two Families and Review," *Surg Neurol*, 1991, pp. 49-53, vol. 35.

Keltner, J. L. et al. "Myotonic Pupils in Charcot-Marie-Tooth Disease. Successful Relief of Symptoms With 0.025% Pilocarpine," *Arch of Ophthalmol*, Nov. 1975, pp. 1141-1148, vol. 93.

Stella, V. J. et al. "Prodrug strategies to overcome poor water solubility" *Advanced Drug Delivery Reviews*, 2007, pp. 677-694, vol. 59.

Weimer, L. H. et al. "Medication-induced exacerbation of neuropathy in Charcot Marie Tooth Disease" *Journal of Neurological Sciences*, 2006, pp. 47-54, vol. 242, Nos. 1-2.

SEQUENCE LISTING

<160> NUMBER OF SEQ ID NOS: 16

<210> SEQ ID NO 1
<211> LENGTH: 1816
<212> TYPE: DNA
<213> ORGANISM: Rattus norvegicus
<220> FEATURE:
<221> NAME/KEY: CDS
<222> LOCATION: (208)..(690)

<400> SEQUENCE: 1

```
gagttacagg gagctccacc agagaacatc tcagggagcc tggctggaag cagcagagct      60
ccgagtctgg tctgctgtga gcatccgctg tcctgcgggg agggctccca tccctggctc     120
tcgattgcaa agaaatccaa gcggaggaag ggcgtacacc attggtctgg cacgctccac     180
cgagcccgag cccaactccc agccacc atg ctt cta ctc ttg ttg ggg atc ctg     234
                                Met Leu Leu Leu Leu Leu Gly Ile Leu
                                  1               5 ttc ctt cac atc gcg gtg cta gtg ttg ctc ttc gtc tcc acc atc gtc       282
Phe Leu His Ile Ala Val Leu Val Leu Leu Phe Val Ser Thr Ile Val
 10                  15                  20                  25 agc caa tgg ctc gag ggc aat gga cac agg act gat ctc tgg cag aac       330
Ser Gln Trp Leu Glu Gly Asn Gly His Arg Thr Asp Leu Trp Gln Asn
                 30                  35                  40 tgt acc aca tcc gcc ttg gga gcc gtc cag cac tgc tac tcc tca tct       378
Cys Thr Thr Ser Ala Leu Gly Ala Val Gln His Cys Tyr Ser Ser Ser
             45                  50                  55 gtg agc gaa tgg ctt cag tct gtc cag gcc acc atg atc ctg tct gtc       426
Val Ser Glu Trp Leu Gln Ser Val Gln Ala Thr Met Ile Leu Ser Val
         60                  65                  70 atc ttc agc gtc ctg tcc ctg ttc ctg ttc tgc cag ctc ttc act           474
Ile Phe Ser Val Leu Ser Leu Phe Leu Phe Cys Gln Leu Phe Thr
     75                  80                  85 ctc acc aaa ggc ggc cgc ttt tac atc act gga gtc ttc caa atc ctt       522
Leu Thr Lys Gly Gly Arg Phe Tyr Ile Thr Gly Val Phe Gln Ile Leu
 90                  95                 100                 105 gct ggt ctg tgt gtg atg agt gca gcg gcc atc tac aca gtg aga cac       570
Ala Gly Leu Cys Val Met Ser Ala Ala Ala Ile Tyr Thr Val Arg His
                110                 115                 120 agt gag tgg cat gtc aac aac gac tac tcc tat ggc ttt gct tac atc       618
Ser Glu Trp His Val Asn Asn Asp Tyr Ser Tyr Gly Phe Ala Tyr Ile
            125                 130                 135 ctg gcc tgg gtg gct ttc ccg ctg gcc ctc ctt agt ggc atc atc tac       666
Leu Ala Trp Val Ala Phe Pro Leu Ala Leu Leu Ser Gly Ile Ile Tyr
        140                 145                 150
```

```
gtg atc ctg cgg aaa cgc gaa tga ggcgcccgac gcaccatccg tctaggctct      720
Val Ile Leu Arg Lys Arg Glu
    155             160 gagcgtgcat agggtacaca gggagggagg aaggaaacca gaaaaccaaa ccaaccaacc      780
caaaagagct agcccccaaa cccaaacgca agccaaacca aacagaacac agttgagtgg      840
ggattgctgt cgattgaaga tgtatataat atctatggtt tataaaacct atttataaca      900 cttttacat acatgtacat aggattgttt gcttttatg ttgaccgtca gcctcgtgtt       960
gaatcttaaa cgactctaca tcctaaacact ataaccaagc tcagtatttt cgttttgttt     1020 cgttttttc atcttttgt tttgctcaga cataaaaaaa aaaaaatcca cgtggccccc       1080
tttcatctga aagcagatcc ctccctccca ttcaacctca taggataacc aaagtgcggg      1140
gacaaacccc agatggccag aggttcacac tatgggtgac ccagtgaatt tagcaggaat      1200
aatccgctgc ccgaatcaat gtgtgaagcc ctaagcactc acagacgaaa cgccctgacc      1260
agagccctct gcgaaaccaa tagctggtgg ctgcggaaca cttgaccctg aaggcggagt      1320
actggggcca catgtttaaa tgagacgtca gagacaagca atctgtgaaa tggtgctata      1380
gatttaccat tccttgttat tactaatcat ttaaaccact cactggaaac tcaattaaca      1440
gttttatgac ctacagcaga acagagaccc gatacaaacg gttcgtaact gctttcgtac      1500
atagctaggc tgttgttatt actacaataa ataaatctca aagccttcgt cactcccaca      1560
gttttctcac ggtcggagca tcaggacgag cgtctagacc cttgggacta gcaaattccc      1620 tggcttctg ggtctagagt gttctgtgcc tccaaggact gtctagcgat gacttgtatt       1680
ggccaccaac tgtagatgta tatacggtgt ccttctgatg ctaagactcc agacctttct      1740
tggttttgct tgcttttctct gattttatac caactgtgtg gactaagatg cattaaaata     1800
aacatcagag taactc                                                      1816

<210> SEQ ID NO 2
<211> LENGTH: 160
<212> TYPE: PRT
<213> ORGANISM: Rattus norvegicus

<400> SEQUENCE: 2

Met Leu Leu Leu Leu Gly Ile Leu Phe Leu His Ile Ala Val Leu
1               5                   10                  15

Val Leu Leu Phe Val Ser Thr Ile Val Ser Gln Trp Leu Glu Gly Asn
                20                  25                  30

Gly His Arg Thr Asp Leu Trp Gln Asn Cys Thr Thr Ser Ala Leu Gly
            35                  40                  45

Ala Val Gln His Cys Tyr Ser Ser Val Ser Glu Trp Leu Gln Ser
        50                  55                  60

Val Gln Ala Thr Met Ile Leu Ser Val Ile Phe Ser Val Leu Ser Leu
65                  70                  75                  80

Phe Leu Phe Phe Cys Gln Leu Thr Leu Thr Lys Gly Gly Arg Phe
                85                  90                  95

Tyr Ile Thr Gly Val Phe Gln Ile Leu Ala Gly Leu Cys Val Met Ser
            100                 105                 110

Ala Ala Ala Ile Tyr Thr Val Arg His Ser Glu Trp His Val Asn Asn
        115                 120                 125

Asp Tyr Ser Tyr Gly Phe Ala Tyr Ile Leu Ala Trp Val Ala Phe Pro
    130                 135                 140

Leu Ala Leu Leu Ser Gly Ile Ile Tyr Val Ile Leu Arg Lys Arg Glu
```

```
<210> SEQ ID NO 3
<211> LENGTH: 17
<212> TYPE: DNA
<213> ORGANISM: Artificial sequence
<220> FEATURE:
<223> OTHER INFORMATION: Forward primer_rat PMP22

<400> SEQUENCE: 3
ggaaacgcga atgaggc                                                    17

<210> SEQ ID NO 4
<211> LENGTH: 19
<212> TYPE: DNA
<213> ORGANISM: Artificial sequence
<220> FEATURE:
<223> OTHER INFORMATION: Reverse primer_rat PMP22

<400> SEQUENCE: 4
gttctgtttg gtttggctt                                                  19

<210> SEQ ID NO 5
<211> LENGTH: 690
<212> TYPE: DNA
<213> ORGANISM: Rattus norvegicus
<220> FEATURE:
<221> NAME/KEY: CDS
<222> LOCATION: (15)..(626)

<400> SEQUENCE: 5
ggcggctgcc gaag atg gcg gag ggg cag gtt cta gta ttg gat ggc cgg       50
                Met Ala Glu Gly Gln Val Leu Val Leu Asp Gly Arg
                 1               5                  10 ggc cat ctt ctg ggc cgc ctg gcg gcc att gtg gcc aag cag gta ctg       98
Gly His Leu Leu Gly Arg Leu Ala Ala Ile Val Ala Lys Gln Val Leu
         15                  20                  25 ctg ggc cga aag gtg gtg gtt gta cgc tgt gag ggc atc aac att tct      146
Leu Gly Arg Lys Val Val Val Val Arg Cys Glu Gly Ile Asn Ile Ser
 30                  35                  40 gga aat ttc tac aga aac aag tta aag tat ctg gcc ttt ctc cga aag      194
Gly Asn Phe Tyr Arg Asn Lys Leu Lys Tyr Leu Ala Phe Leu Arg Lys
45                  50                  55                  60 cgg atg aac acc aac ccg tct cga ggc ccc tac cac ttc cga gcc cca      242
Arg Met Asn Thr Asn Pro Ser Arg Gly Pro Tyr His Phe Arg Ala Pro
                 65                  70                  75 agc cgc att ttt tgg cgc act gtg cga ggc atg ctg ccg cac aag acc      290
Ser Arg Ile Phe Trp Arg Thr Val Arg Gly Met Leu Pro His Lys Thr
             80                  85                  90 aaa aga ggc cag gct gcc ctg gaa cgc ctc aag gtg ttg gat ggg atc      338
Lys Arg Gly Gln Ala Ala Leu Glu Arg Leu Lys Val Leu Asp Gly Ile
         95                 100                 105 cct cca ccc tat gac aag aaa aag cgg atg gtg gtc cct gct gcc ctc      386
Pro Pro Pro Tyr Asp Lys Lys Lys Arg Met Val Val Pro Ala Ala Leu
110                 115                 120 aag gtt gtg cgg ctg aag cct acc aga aag ttt gct tac ctg ggg cgt      434
Lys Val Val Arg Leu Lys Pro Thr Arg Lys Phe Ala Tyr Leu Gly Arg
125                 130                 135                 140 ctg gct cat gag gtc ggg tgg aag tac cag gca gtg aca gct act ctg      482
Leu Ala His Glu Val Gly Trp Lys Tyr Gln Ala Val Thr Ala Thr Leu
                145                 150                 155 gag gag aaa cgg aag gaa aag gca aag atc cat tac cgg aag aag aag      530
Glu Glu Lys Arg Lys Glu Lys Ala Lys Ile His Tyr Arg Lys Lys Lys
```

```
                    160                 165                 170
cag ctc ttg agg cta agg aaa cag gca gaa aag aat gtg gag aag aaa      578
Gln Leu Leu Arg Leu Arg Lys Gln Ala Glu Lys Asn Val Glu Lys Lys
        175                 180                 185 atc tgc aag ttc aca gag gtc ctc aag acc aat gga ctc ttg gtg tga      626
Ile Cys Lys Phe Thr Glu Val Leu Lys Thr Asn Gly Leu Leu Val
    190                 195                 200 acccaataaa gactgtttgt gcctcaaaaa aaaaaaaaaa aaaaaaaaaa aaaaaaaaaa    686
aaaa                                                                 690

<210> SEQ ID NO 6
<211> LENGTH: 203
<212> TYPE: PRT
<213> ORGANISM: Rattus norvegicus

<400> SEQUENCE: 6

Met Ala Glu Gly Gln Val Leu Val Leu Asp Gly Arg Gly His Leu Leu
1               5                   10                  15

Gly Arg Leu Ala Ala Ile Val Ala Lys Gln Val Leu Leu Gly Arg Lys
                20                  25                  30

Val Val Val Val Arg Cys Glu Gly Ile Asn Ile Ser Gly Asn Phe Tyr
            35                  40                  45

Arg Asn Lys Leu Lys Tyr Leu Ala Phe Leu Arg Lys Arg Met Asn Thr
        50                  55                  60

Asn Pro Ser Arg Gly Pro Tyr His Phe Arg Ala Pro Ser Arg Ile Phe
65                  70                  75                  80

Trp Arg Thr Val Arg Gly Met Leu Pro His Lys Thr Lys Arg Gly Gln
                85                  90                  95

Ala Ala Leu Glu Arg Leu Lys Val Leu Asp Gly Ile Pro Pro Pro Tyr
            100                 105                 110

Asp Lys Lys Lys Arg Met Val Val Pro Ala Ala Leu Lys Val Val Arg
        115                 120                 125

Leu Lys Pro Thr Arg Lys Phe Ala Tyr Leu Gly Arg Leu Ala His Glu
    130                 135                 140

Val Gly Trp Lys Tyr Gln Ala Val Thr Ala Thr Leu Glu Glu Lys Arg
145                 150                 155                 160

Lys Glu Lys Ala Lys Ile His Tyr Arg Lys Lys Gln Leu Leu Arg
                165                 170                 175

Leu Arg Lys Gln Ala Glu Lys Asn Val Glu Lys Lys Ile Cys Lys Phe
            180                 185                 190

Thr Glu Val Leu Lys Thr Asn Gly Leu Leu Val
        195                 200

<210> SEQ ID NO 7
<211> LENGTH: 17
<212> TYPE: DNA
<213> ORGANISM: Artificial sequence
<220> FEATURE:
<223> OTHER INFORMATION: Forward primer_RPL13A

<400> SEQUENCE: 7
ctgccctcaa ggttgtg                                                   17

<210> SEQ ID NO 8
<211> LENGTH: 21
<212> TYPE: DNA
<213> ORGANISM: Artificial sequence
<220> FEATURE:
```

<223> OTHER INFORMATION: Reverse primer_RPL13A

<400> SEQUENCE: 8
cttcttcttc cggtaatgga t                                    21

<210> SEQ ID NO 9
<211> LENGTH: 22
<212> TYPE: DNA
<213> ORGANISM: Artificial sequence
<220> FEATURE:
<223> OTHER INFORMATION: FRET probe_Pmp22_fluoresceine labelled

<400> SEQUENCE: 9
gctctgagcg tgcatagggt ac                                   22

<210> SEQ ID NO 10
<211> LENGTH: 19
<212> TYPE: DNA
<213> ORGANISM: Artificial sequence
<220> FEATURE:
<223> OTHER INFORMATION: FRET probe_Rpl13A_fluoresceine labelled

<400> SEQUENCE: 10
tcgggtggaa gtaccagcc                                       19

<210> SEQ ID NO 11
<211> LENGTH: 25
<212> TYPE: DNA
<213> ORGANISM: Artificial sequence
<220> FEATURE:
<223> OTHER INFORMATION: FRET probe_Pmp22_rhodamine labelled

<400> SEQUENCE: 11
agggagggag gaaggaaacc agaaa                                25

<210> SEQ ID NO 12
<211> LENGTH: 28
<212> TYPE: DNA
<213> ORGANISM: Artificial sequence
<220> FEATURE:
<223> OTHER INFORMATION: FRET probe_Rpl13A_rhodamine labelled

<400> SEQUENCE: 12
tgacagctac tctggaggag aaacggaa                             28

<210> SEQ ID NO 13
<211> LENGTH: 19
<212> TYPE: DNA
<213> ORGANISM: Artificial sequence
<220> FEATURE:
<223> OTHER INFORMATION: Primer 1_Sry-specific

<400> SEQUENCE: 13
gagagaggca caagttggc                                       19

<210> SEQ ID NO 14
<211> LENGTH: 19
<212> TYPE: DNA
<213> ORGANISM: Artificial sequence
<220> FEATURE:
<223> OTHER INFORMATION: Primer 2_Sry-specific

<400> SEQUENCE: 14
gcctcctgga aaagggcc                                        19

```
<210> SEQ ID NO 15
<211> LENGTH: 19
<212> TYPE: DNA
<213> ORGANISM: Artificial sequence
<220> FEATURE:
<223> OTHER INFORMATION: Forward primer _PMP22 transgene

<400> SEQUENCE: 15
gacaaacccc agacagttg                                                    19

<210> SEQ ID NO 16
<211> LENGTH: 19
<212> TYPE: DNA
<213> ORGANISM: Artificial sequence
<220> FEATURE:
<223> OTHER INFORMATION: Reverse primer_PMP22 transgene

<400> SEQUENCE: 16
ccagaaagcc agggaactc                                                    19
```

COMBINATION OF PILOCARPIN AND METHIMAZOL FOR TREATING CHARCOT-MARIETOOTH DISEASE AND RELATED DISORDERS

CROSS-REFERENCE TO RELATED APPLICATIONS

This application is a continuation of U.S. application Ser. No. 12/999,125, filed Aug. 3, 2011, which is the U.S. national stage application of International Patent Application No. PCT/EP2009/057544, filed Jun. 17, 2009.

The Sequence Listing for this application is labeled "Seq-List.txt" which was created on Dec. 14, 2010 and is 13 KB. The entire contents of the sequence listing is incorporated herein by reference in its entirety.

The present invention relates to compositions and methods for the treatment of the Charcot-Marie-Tooth disease and related disorders.

Charcot-Marie-Tooth disease ("CMT") is an orphan genetic peripheral poly neuropathy. Affecting approximately 1 in 2,500 individuals, this disease is the most common inherited disorder of the peripheral nervous system. Its onset typically occurs during the first or second decade of life, although it may be detected in infancy. Course of disease is chronic with gradual neuromuscular degeneration. The disease is invalidating with cases of accompanying neurological pain and extreme muscular disability. CMT is one of the best studied genetic pathologies with approximately 30,000 cases in France. While a majority of CMT patients harbour a duplication of a chromosome 17 fragment containing a myelin gene: PMP22 (form CMT1A), two dozens of genes have been implicated in different forms of CMT. Accordingly, although monogenic in origin, this pathology manifests clinical heterogeneity due to possible modulator genes. The genes mutated in CMT patients are clustering around tightly connected molecular pathways affecting differentiation of Schwann cells or neurons or changing interplay of these cells in peripheral nerves.

PMP22 is a major component of myelin expressed in the compact portion of essentially all myelinated fibers in the peripheral nervous system and is produced predominantly by Schwann cells. Furthermore, PMP22 gene is assumed to be involved in the development of neoplasia in patients with neurofibromatosis, an autosomal dominant disorder characterized by cafe-au-lait spots and fibromatous tumors of the skin. A modest, 1.5-fold overexpression of a normal PMP22 protein is also observed in Schwann cells heterozygous for the duplication in CMT patients (in some rare cases, CMT1A-like phenotype can be also linked to structural mutations in PMP22 protein) (Lupski et al., 1992; Suter et al., 1992; Roa et al., 1993; Thomas et al., 1997; Suter & Scherer, 2003; Nave & Sereda, 2007). Direct evidence that abnormal PMP22 gene dosage causes a CMT1A-like phenotype was provided by transgenic experiments in rodent models with overexpression of PMP22 protein (Niemann et al., 1999; Perea et al., 2001; Robaglia-Schlupp et al., 2002; Meyer et al., 2006; Sereda & Nave, 2006).

Furthermore, therapeutic interventions with inhibitor of progesterone receptor and ascorbic acid decreased this expression in the transgenic animals ameliorating or slowing the progression of disease phenotype (Sereda et al., 2003; Passage et al., 2004; Meyer zu Horste et al., 2007).

Bassi and al., 1978, relates to the use of methimazole in the treatment of the thyrotoxicose associated with neuropathy and encephalomyelitis.

WO 00/20024 of Celtrix concerns the use of methimazole for alleviating symptoms of an IGF-dependent disorder which is a thyroid disorder.

WO2004/019938 relates to the use of pilocarpine in the treatment of syndromes of neuropathic pain.

The use of pilocarpine, alone, for the treatment of myotonic papillary abnormalities was suggested by Keltner et al., 1975. However, the use of pilocarpine for treatment of CMT was not described. Moreover, the use of pilocarpine in combination with any other compound was not suggested either.

In conclusion, there is a need for efficient and approved therapy for treating CMT disease.

SUMMARY OF THE INVENTION

The purpose of the present invention is to provide new therapeutic approaches for treating CMT and related disorders. More specifically, the inventors have identified novel combination therapies which effectively affect pathways leading to CMT and related disorders, and represent new approaches for the treatment of these disorders. The invention therefore provides novel combination products and compositions, as well as the uses thereof for treating CMT disease and related disorders.

An object of this invention more specifically relates to the use of a combination of compounds for (the manufacture of a medicament for) treating CMT or a related disorder, wherein said combination of compounds is selected from a muscarinic receptor agonist or a prodrug thereof and an inhibitor of thyroid hormone synthesis or a prodrug thereof.

Another object of this invention resides in a combination product comprising a muscarinic receptor agonist and an inhibitor of thyroid hormone synthesis, or a prodrug thereof, for a grouped or separate administration to a subject, simultaneously or sequentially.

The invention also relates to a pharmaceutical composition comprising a muscarinic receptor agonist and an inhibitor of thyroid hormone synthesis, or a prodrug thereof, and a pharmaceutically acceptable carrier or excipient.

In a most preferred embodiment, the muscarinic receptor agonist is (3S,4R)-3-ethyl-4-[(3-methylimidazol-4-yl)methyl]oxolan-2-one (CAS 92-13-7, which is an active agent of pilocarpine pharmaceutical), or a prodrug thereof.

Furthermore in a most preferred embodiment, the inhibitor of thyroid hormone synthesis further displays activity in prostaglandin signalling. Preferred examples of such compounds include 1-methyl-3H-imidazole-2-thione (CAS 60-56-0, which is an active agent of methimazole pharmaceutical), or a prodrug thereof, such as carbimazole.

In another embodiment, the invention relates to a composition comprising a muscarinic receptor agonist and an inhibitor of thyroid hormone synthesis for the treatment of CMT in a subject, wherein the treatment further comprises a step of determining whether the patient has CMT1A.

In this regard, a particular object of this invention relates to a composition comprising pilocarpine, or a prodrug thereof, and methimazole, or a prodrug thereof and, optionally, a pharmaceutically acceptable carrier or excipient. As shown in the examples, such a combination allows to effectively treat CMT in recognized animal models.

The products or compositions of this invention may further comprise at least one additional active compound, preferentially selected from the group consisting of rapamycin, baclofen, sorbitol, mifepristone, naltrexone, flurbiprofen and ketoprofen.

In a preferred embodiment, the composition according to the invention comprises at least:
pilocarpine, methimazole and mifepristone;
pilocarpine, methimazole and baclofen; or
pilocarpine, methimazole and sorbitol.

In another preferred embodiment, the composition according to the invention comprises at least:
pilocarpine, methimazole, mifepristone, baclofen and sorbitol; or
pilocarpine, methimazole, mifepristone, baclofen, sorbitol and naltrexone.

In other embodiments, the present invention relates to a product or composition comprising methimazole, pilocarpine and two additional active compounds, preferably mifepristone and sorbitol.

In other embodiments, the present invention relates to a product or composition comprising methimazole, pilocarpine and three additional active compounds, preferably:
mifepristone, baclofen and sorbitol; or
mifepristone, sorbitol and rapamycin; or
mifepristone, sorbitol and ketoprofen; or
mifepristone, sorbitol and flurbiprofen.

In other embodiments, the present invention relates to a product or composition comprising methimazole, pilocarpine and four additional active compounds, preferably:
mifepristone, sorbitol, baclofen and naltrexone;
mifepristone, sorbitol, baclofen and rapamycin;
mifepristone, sorbitol, naltrexone and rapamycin.

In other embodiments, the invention relates to a product or composition, which comprises any drug combination as disclosed in Table 1.

In other specific embodiments, the present invention relates to a product or composition comprising:
methimazole and baclofen; or
methimazole and cevimeline.

In another embodiment, the invention also relates to a product or composition comprising pilocarpine and propylthiouracil.

Another object of the invention relates to the use of a combination of pilocarpine with methimazole or these two compounds alone, or in combination(s) with other compounds enhancing their effect for the (manufacture of a medicament for the) treatment of CMT or a related disorder.

Another object of the invention relates to the use of a combination of pilocarpine with methimazole or these two compounds alone, or in combination(s) with other compounds enhancing their effect for the (manufacture of a medicament for the) treatment of toxic neuropathy.

Another object of the invention relates to the use of a combination of pilocarpine with methimazole or these two compounds alone, or in combination(s) with other compounds enhancing their effect for the (manufacture of a medicament for the) treatment of ALS (Amyotrophic Lateral Sclerosis).

Preferably, the compounds enhancing the effect of pilocarpine and methimazole combination, for the treatment of CMT, are selected from the group consisting of mifepristone, baclofen, sorbitol, naltrexone, rapamycin, flurbiprofen and ketoprofen.

In a variant, a pilocarpine and methimazole mixture is used, for the treatment of CMT or a related disorder, in combination with one additional active compound, preferably mifepristone or baclofen.

In another variant a pilocarpine and methimazole mixture is used in combination with two additional active compounds, preferably mifepristone and sorbitol.

In another variant a pilocarpine and methimazole mixture is used in combination with three additional active compounds, preferably consisting of mifepristone and sorbitol in combination with a third compound selected from baclofen, rapamycin, ketoprofen or furbiprofen.

In another variant a pilocarpine and methimazole mixture is used in combination with four additional active compounds, preferably mifepristone, sorbitol, baclofen and naltrexone or rapamycin; or mifepristone, sorbitol, naltrexone and rapamycin.

The invention further provides a method for treating CMT or a related disorder, particularly CMT, comprising administering to a subject in need thereof an effective amount of combination of a muscarinic receptor agonist, or a prodrug thereof, and an inhibitor of thyroid hormone synthesis, or a prodrug thereof.

The invention further relates to a method of treating CMT in a subject, comprising administering to the subject an effective amount of a combination of pilocarpine, or a prodrug thereof, and methimazole, or a prodrug thereof.

The invention also relates to a method of treating CMT in a subject, comprising administering to the subject an effective amount of a combination of pilocarpine and methimazole with at least one additional active compound, preferentially selected from the group of rapamycin, baclofen, sorbitol, mifepristone, naltrexone, flurbiprofen and ketoprofen.

In variants, the present invention also relates to a method of treating CMT in a subject, comprising administering to the subject an effective amount of a combination of:
pilocarpine, methimazole and at least one additional active compound which is selected from baclofen, mifepristone, sorbitol and naltrexone;
pilocarpine, methimazole and baclofen;
pilocarpine, methimazole and mifepristone;
pilocarpine, methimazole, mifepristone, sorbitol and baclofen;
pilocarpine, methimazole, mifepristone, sorbitol and rapamycin;
pilocarpine, methimazole, mifepristone, sorbitol and ketoprofen;
pilocarpine, methimazole, mifepristone, sorbitol and flurbiprofen;
pilocarpine, methimazole, mifepristone, sorbitol, baclofen, and naltrexone;
pilocarpine, methimazole, mifepristone, sorbitol, baclofen and rapamycin;
pilocarpine, methimazole, mifepristone, sorbitol, naltrexone and rapamycin;
methimazole and baclofen;
methimazole and cevimeline; or
pilocarpine and propylthiouracil.

The invention may be used for treating CMT or a related disorder in any mammalian subject, particularly human subjects. It is particularly suited for treating CMT1a.

In this respect, a specific object of this invention is a method of treating CMT1a in a subject, comprising administering to the subject an effective amount of a combination of pilocarpine, or a prodrug thereof, and methimazole, or a prodrug.

A further object of this invention is a method of treating CMT1a, the method comprising (1) assessing whether a subject has CMT1a and (2) treating the subject having CMT1a with an effective amount of a combination of pilocarpine, or a prodrug thereof, and methimazole, or a prodrug thereof. Determining whether a subject has CMT1a can be done by various tests known per se in the art, such as DNA assays.

LEGEND TO THE FIGURES

FIG. 1: Relative levels are represented as % of PMP22 mRNA expression in primary rat Schwann cells treated for 24 hrs with compounds A and B. On the left is represented % of PMP22 mRNA level, 24 hrs after 1 mM or 1 µM of compound A (methimazole) addition. It is observed that PMP22 mRNA is significantly decreased in primary Schwann cells, and that the lower dose of compound A induces the most important PMP22 down-regulation. *: $p<0.05$; ***: $p<0.001$; significantly different from control (pairwise student t test). On the right, exposed 24 hrs to compound B (pilocarpine), PMP22 mRNA level of expression is significantly down-regulated in primary Schwann cells even at very low doses (10 nM and 50 nM). Similarly, we observed that compound B (1 µM) significantly decrease PMP22 protein level of expression after 24 hrs of incubation, by 38% in primary Schwann cells. This effect is still significant after 48 hrs of incubation (−18%, $p<0.001$).

Figure 2:
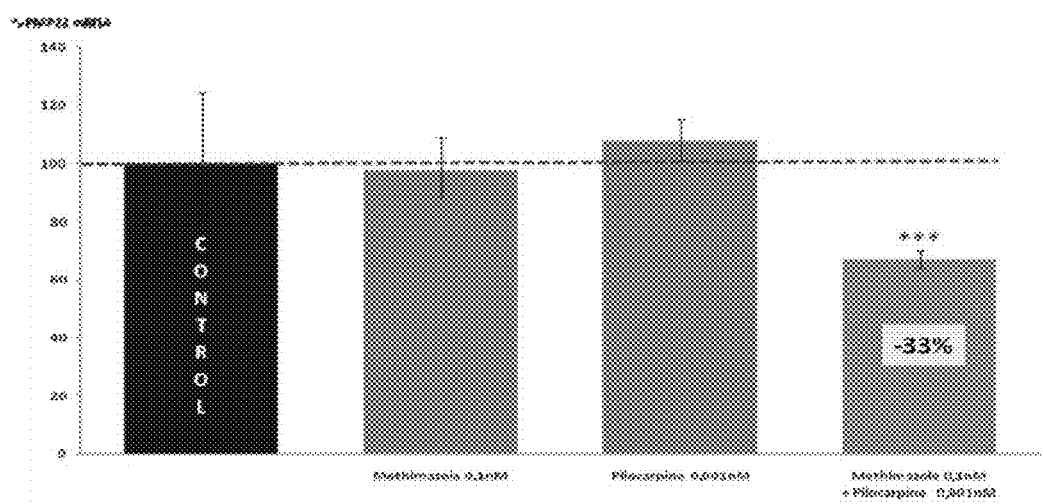

FIG. 2: Effect of selected drugs on PMP22 mRNA level of expression quantified by RT-Q-PCR in RT4-D6P2T schwannoma cells. ***: $p<0.0001$: significantly different from control (=no drug). Bilateral Student's t test on ΔΔCt values.

Figure 3:
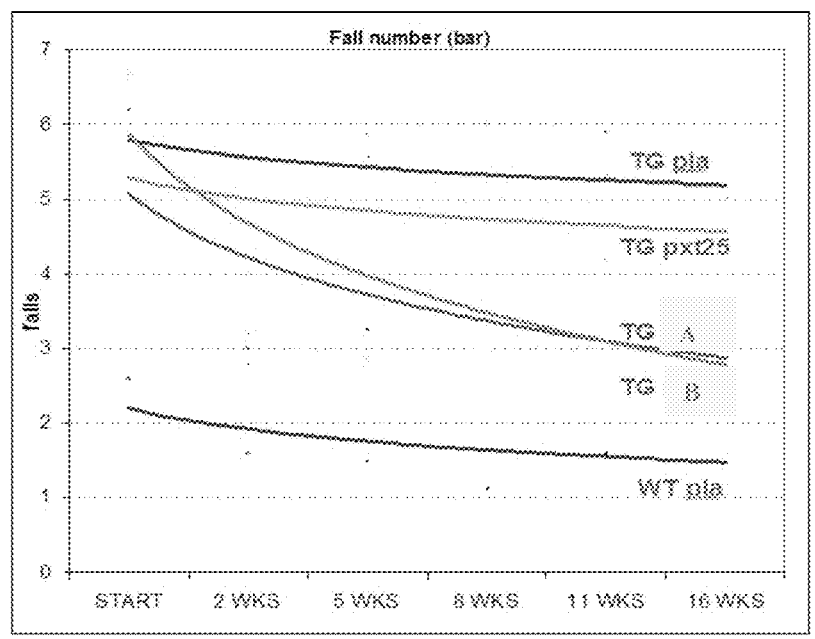

FIG. 3: Results of the motor assessment of the female rats in the Bar-test throughout the treatment study presented in form of trends. WTplacebo: normal rats treated with placebo; TGplacebo: control transgenic rats treated with placebo, TGptx25: transgenic rats treated with negative control substance, TGA: transgenic rats force fed with daily dose of 0.2 mg/kg of methimazole; TGB: transgenic rats treated with daily dose of 0.35 mg/kg of pilocarpine.

Figure 4:
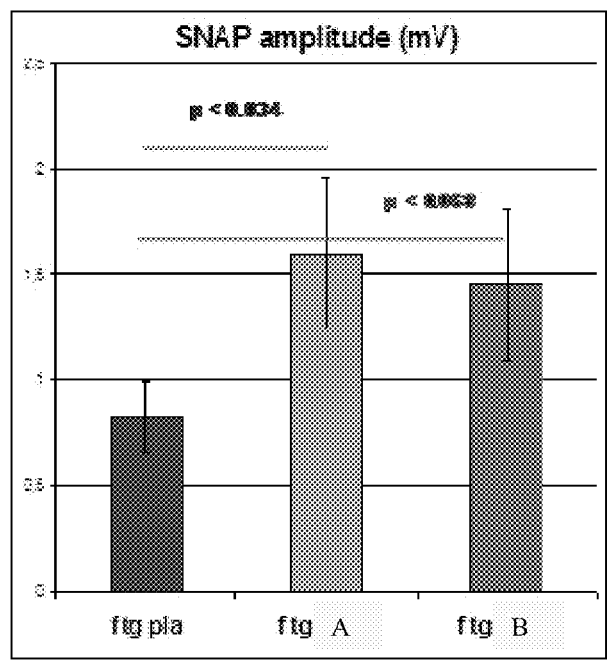

FIG. 4: Electrophysiological assessment of the sensitive nerve potential amplitude in CMT rats treated with drugs during 20 weeks. TGplacebo: control transgenic rats treated with placebo, TGptx25: transgenic rats treated with negative control substance, TGA: transgenic rats treated with daily dose of 0.2 mg/kg of methimazole; TGB: transgenic rats treated with daily dose of 0.35 mg/kg pilocarpine.

Figure 5:
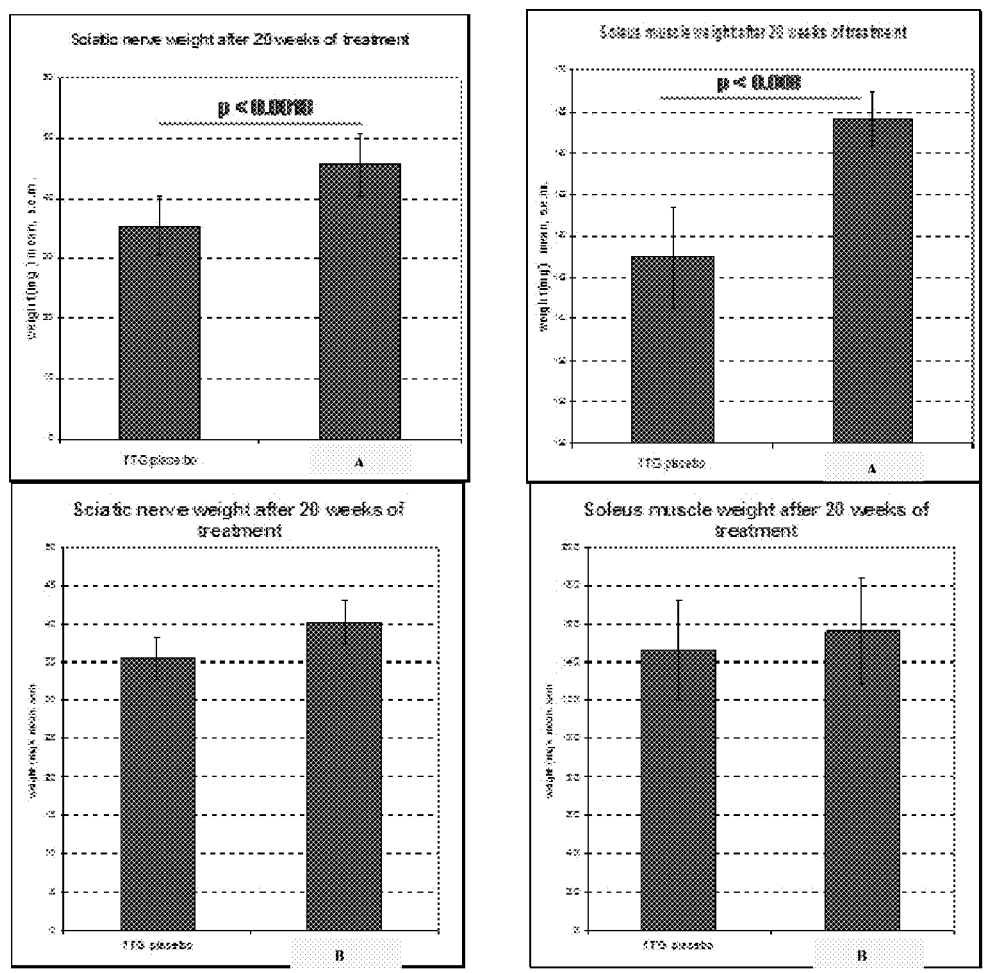

FIG. 5: The analysis of the post-mortem samples obtained from the animals treated with drugs as described in the legend to FIG. 3. The rats treated with drugs and placebo during 20 weeks, were deeply anesthetized and the entire sciatic nerves and soleus muscles were carefully sampled and weighted. The graphs present the mean values of these measurements.

Figure 6:
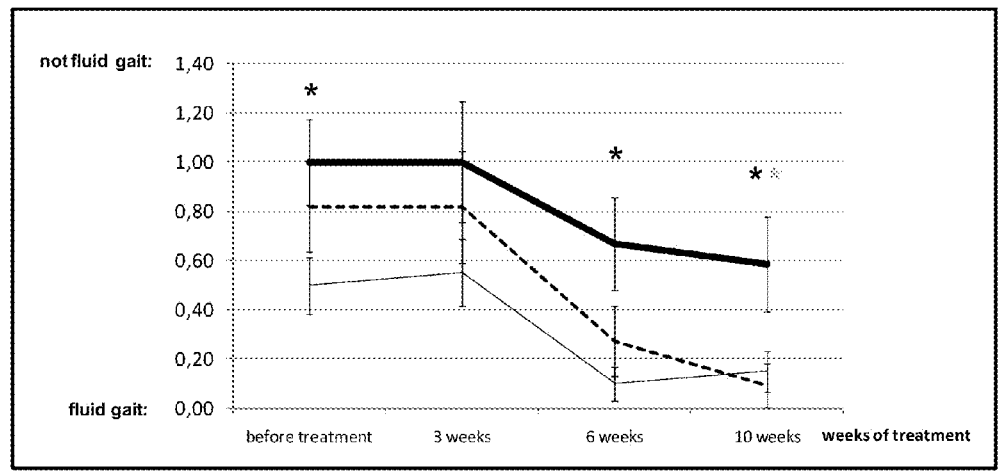

FIG. 6: Positive effect of the Mix1 in the gait evaluation test (female rats); black line represents control rats treated with placebo; black bold line represents transgenic rats treated with placebo; dotted line represents transgenic rats treated with Mix1. * $p<0.05$; black *: wt placebo vs tg placebo; grey *: tg placebo vs tg mix1. Statistics are realised with the Student bilateral test; mean is represented±s.e.m.

Figure 7:
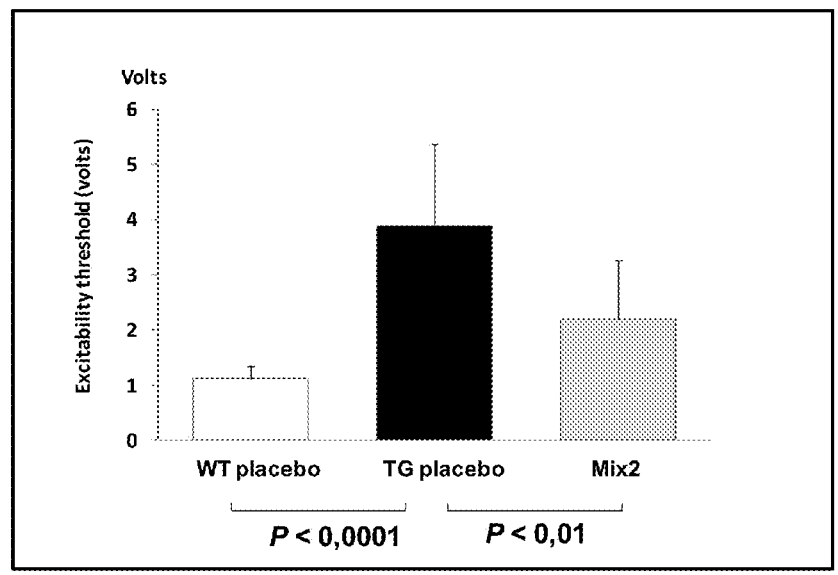

FIG. 7: Positive effect of Mix2 on the excitability threshold of the caudal nerve (white bars represent control male rats treated with placebo; black bars represent transgenic male rats treated with placebo; grey bars represent transgenic male rats treated with Mix2. Statistics are realised with the Student bilateral test; mean is represented±s.e.m.

Figure 8:
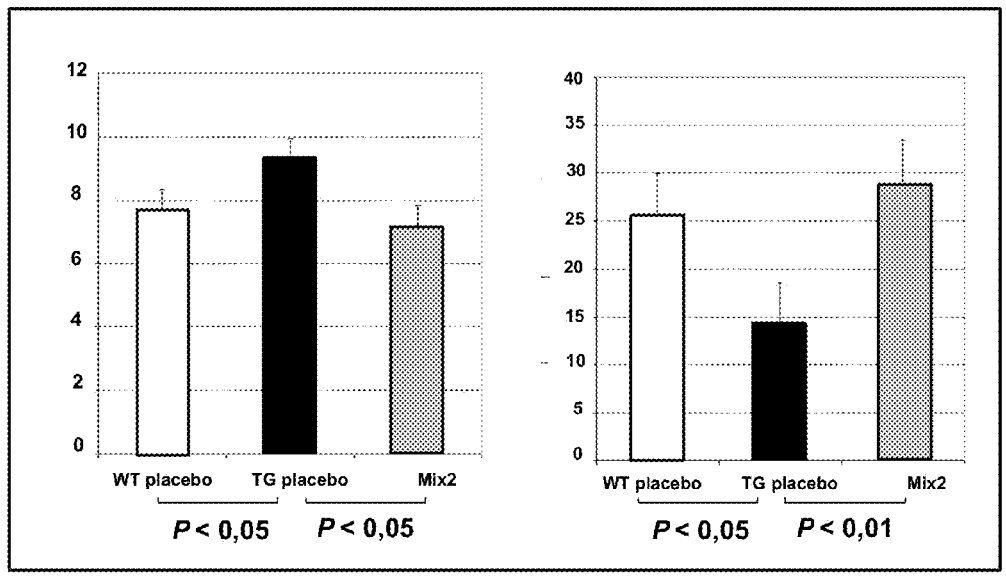

FIG. 8: Positive effect of Mix2 after 4 weeks of treatment in the bar test (white bars represent control male rats treated with placebo; black bars represent transgenic male rats treated with placebo; grey bars represent transgenic male rats treated with Mix2). Statistics are realised with the Student bilateral test; mean is represented±s.e.m.

Figure 9:
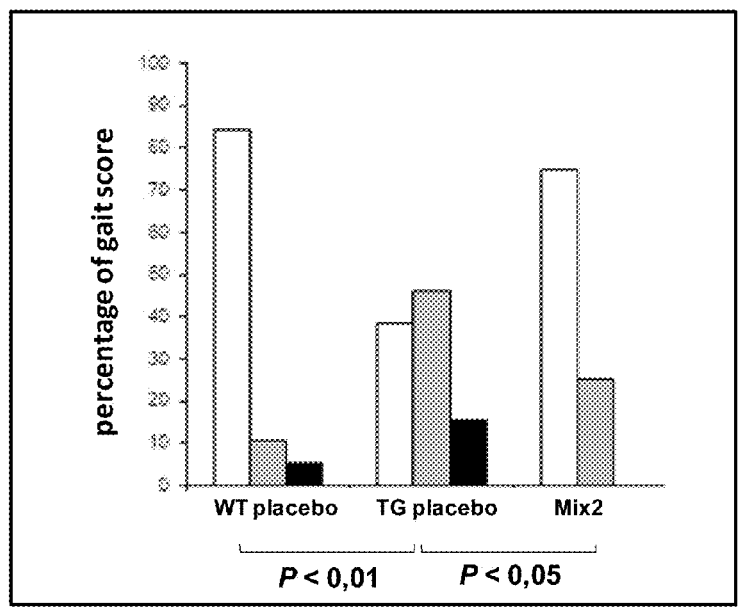

FIG. 9: Positive effect on gait of Mix2 after 3 weeks of treatment (white bars represent the percentage of male rats in each group walking with a fluid gait; grey bars represent the not fluid gait; black bars represent the incapacity). Statistics are realised with the Student bilateral test.

Figure 10:
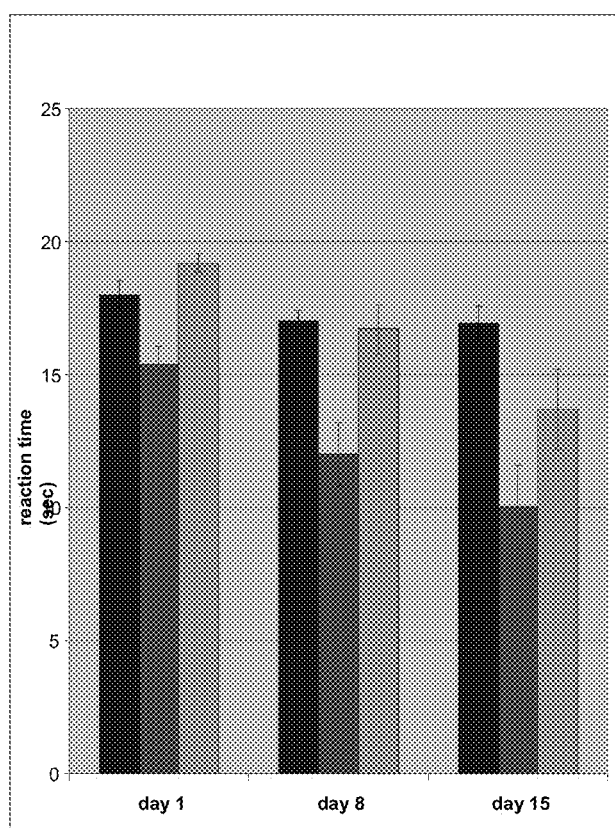

FIG. 10: Anti-allodynic effect in chronic OXALPN model. In blue are shown the reaction times in acetone test for control animals, in red oxaliplatin treated animals, in green color the animals treated with oxaliplatin and mix 2.

DETAILED DESCRIPTION OF THE INVENTION

The present invention provides new therapeutic approaches for treating CMT or related disorders. The invention discloses novel compositions made from combinations of known drugs and their new use for effective correction of such diseases and may be used in any mammalian subject.

Within the context of the present invention, the term "CMT related disorder" designates other peripheral neuropathies both hereditary and acquired.

The major form of CMT, CMT1A, is caused by duplication of PMP22 gene. PMP22 is a major component of myelin expressed in the compact portion of essentially all myelinated fibers in the peripheral nervous system. PMP22 protein interacts with another structural myelin protein P0, and therefore, the altered PMP22/P0 protein ratio might influence the compaction of myelin sheaths (Vallat et al., 1996; D'Urso et al., 1999). As demonstrated by in vitro studies, PMP22 protein is also involved in the regulation of cell spreading in a Rho-dependent manner and thus could affect axonal ensheathment (Brancolini et al., 1999). Moreover, PMP22 forms complexes with α6β4 integrins and could mediate the interaction of Schwann cells with extracellular matrix (Amici et al., 2006; Amici et al., 2007). Furthermore, increased level of PMP22 protein can alter the Arf6-regulated plasma membrane endosomal recycling pathway and lead to accumulation of PMP22 in the late endosomes (Chies et al., 2003). It was also demonstrated that over expressed PMP22 protein perturbs intracellular protein sorting and overloads the protein degradation machinery in Schwann cells (Notterpek et al., 1997; Tobler et al., 2002; Fortun et al., 2003; Fortun et al., 2006; Fortun et al., 2007; Khajavi et al., 2007). Finally, PMP22 is directly involved in the control of cell proliferation and programmed cell death (Sancho et al., 2001; Atanasoski et al., 2002) and mutant PMP22 protein was shown to provoke profound reorganization and the aberrant expression of axonal ion channels (Ulzheimer et al., 2004; Devaux & Scherer, 2005).

Consequently, the term "CMT related disorder" comprises peripheral disorders such as ALS, toxic neuropathies, idiopathic neuropathies, diabetic neuropathy, cancer and HIV induced neuropathies, Guillain-Barré syndrome.

In a preferred embodiment, CMT related disorder designates a neuropathy, such as demyelinating neuropathies, including HNPP (hereditary neuropathy with liability to pressure palsies), CMT1B, CMT1C, CMT1D, CMT1X, CMT2A, CMT2B, CMT2D, CMT2E, CMT2-P0, severe demyelinating neuropathies DSS (Dejerine-Sottas syndrome), CHN (congenital hypomyelinating neuropathy), CMT4A, CMT4B1, CMT4B2, CMT4D, CMT4F, CMT4, AR-CMT2A, HSN1.

The invention is particularly suited for treating CMT1A.

As used herein, "treatment" of a disorder includes the therapy, prevention, prophylaxis, retardation or reduction of pain provoked by the disorder. The term treatment includes in particular the control of disease progression and associated symptoms.

Also, the term compound designates the chemical compounds as specifically named in the application, as well as any pharmaceutically acceptable salt, hydrate, ester, ether, isomers, racemates, conjugates, pro-drugs thereof.

Also, the term "combination" designates a treatment wherein at least two drugs are co-administered to a subject to cause a biological effect. In a combined therapy, the at least two drugs may be administered together or separately, at the same time or sequentially. Also, the at least two drugs may be administered through different routes and protocols.

The invention shows that CMT or a CMT related disorder can be treated by a particular combination of drugs. More specifically, the invention shows that methimazole and pilocarpine compounds, in combination(s), can be used to treat CMT or related disorders. In this regard, the experimental results show that a combination of methimazole and pilocarpine decreases significantly the level of RNA expression of PMP22 gene in rat Schwann cells. Furthermore, PMP22 transgenic rats modelling human CMT disease have been treated daily with combinations containing methimazole and pilocarpine. Significant improvement of behavioural endpoints was observed.

Pilocarpine: (3S,4R)-3-ethyl-4-[(3-methylimidazol-4-yl)methyl]oxolan-2-one

This drug, $C_{11}H_{16}N_2O_2$, has been approved for the treatment of i) symptoms of dry mouth from salivary gland hypofunction caused by radiotherapy for cancer of the head and neck; and ii) the treatment of symptoms of dry mouth in patients with Sjogren's syndrome.

Agonist of muscarinic receptors, it causes smooth muscle fibers contraction (digestive tract, eye, bronchus), stimulates sudoral, salivary, bronchus and gastric secretions. Furthermore, it exhibits a complex cardiovascular action, stimulating both parasympathomimetic (vasodilation) excitoganglionary pathways.

The inventors have demonstrated that pilocarpine, an agonist of muscarinic receptors, decreases expression of the PMP22 protein in Schwann cells in vitro. We propose that stimulation of muscarinic receptors by pilocarpine leads, —likely, through complex set of molecular mechanisms, —to shifting in intracellular balance of Erk/Akt activities, which regulate expression of myelin-associated protein markers in opposite manner, to more pronounced Erk signalling (Ogata et al., 2004).

Without being bound by theory, it is postulated that stimulation of muscarinic receptors can modify activity of Akt and Erk kinases by several concomitant mechanisms (Ma et al., 2004; Anger et al., 2007). For instance, muscarinic receptors can selectively block signalling by IGF-1, but not PDGF receptors, by promoting inhibitory tyrosine dephosphorylation or inhibitory serine phosphorylation of IRS-1 by PKC. Then, muscarinic receptors could mediate intracellular transactivation of ERK signalling through Src-like Fyn kinase; as well, by decreasing activity of adenylate cyclase, muscarinic receptors might be involved in functional regulation of the Akt/Gsk-3β and Erk kinases also through PKA-mediated mechanism. Finally, it was demonstrated that stimulation of muscarinic receptors can—through activation of AMPK—transiently cause dephosphorylation of Akt, and thus decrease intracellular pool of β-catenin (Batty et al., 2004; King et al., 2006).

As a result, other muscarinic receptor agonists could be used as well, such as: Cevimeline (CAS number 107233-08-9), Carbachol (CAS number 51-83-2), Methacholine (CAS numbers 55-92-5) and Bethanechol (CAS number 674-38-4).

Methimazole: 1-methyl-3H-imidazole-2-thione

Methimazole inhibits the production of new thyroid hormones by blocking activity of thyroid peroxidise, converting iodide to iodine and catalyzing the incorporation of the resulting iodide molecule onto the phenol rings of tyrosines. Thus, methimazole can effectively decrease transcriptional activity of thyroid hormone receptors. Additionally, methimazole has been reported to suppress prostaglandin production by attenuating prostaglandin H synthase activity (Zelman et al., 1984). Prostaglandins—through their cognate GPCR receptors—could further augment activity of Akt signalling pathway, which promotes expression of myelin-related proteins (Ogata et al., 2004; Castellone et al., 2006). Accordingly, compounds which both inhibit thyroid hormone synthesis and affect prostaglandin production or signalling are particularly advantageous for use in the present invention.

Other compounds related by action mode to methimazole are carbimazole (prodrug of methimazole—CAS number 22232-54-8) and propylthiouracil (CAS number 51-52-5), and amiodarone (CAS number 1951-25-3).

As disclosed in the examples, compounds methimazole and pilocarpine exert a combined action leading to improved therapeutic effect against CMT, permitting downscaling effective therapeutic doses with diminished secondary effects.

A particular embodiment of the invention resides in a combination therapy for treating CMT or a related disorder, particularly CMT1A, wherein said combination therapy comprises methimazole and pilocarpine compounds and at least a third compound able to enhance the activity of this combination.

Another particular embodiment of the invention resides in a combination therapy for treating ALS, wherein said combination therapy comprises methimazole and pilocarpine compounds and at least a third compound able to enhance the activity of this combination.

Another particular embodiment of the invention resides in a combination therapy for treating toxic neuropathy, wherein said combination therapy comprises methimazole and pilocarpine compounds and at least a third compound able to enhance the activity of this combination.

A particular embodiment of the invention resides in a therapy for treating CMT or a related disorder, wherein compounds methimazole and pilocarpine are used alone.

Another particular embodiment of the invention resides in a therapy for treating CMT or a related disorder, wherein methimazole and/or pilocarpine are used in combination with at least one additional active compound. In a preferred embodiment, the at least one additional compound is selected from the group of compounds listed in Table 1.

Another particular embodiment of the invention resides in a product or composition, which comprises any drug combination as disclosed in Table 1.

Another particular embodiment of the invention resides in a combination therapy for treating CMT or a related disorder, comprising any drug combination as disclosed in Table 1.

Another particular embodiment of the invention resides in a combination therapy for treating ALS, comprising any drug combination as disclosed in Table 1.

Another particular embodiment of the invention resides in a combination therapy for treating toxic neuropathy, comprising any drug combination as disclosed in Table 1.

Therapy according to the invention is performed as drug combination, optionally in conjunction with any other therapy. It may be provided at home, the doctor's office, a clinic, a hospital's outpatient department, or a hospital, so that the doctor can observe the therapy's effects closely and make any adjustments that are needed.

The duration of the therapy depends on the stage of the disease, the age and condition of the patient, and how the patient responds to the treatment.

Additionally, a person having a greater risk of developing an additional neuropathic disorder (e.g., a person who is genetically predisposed to or has, for example, diabetes, or is being under treatment for an oncological condition, etc.) may receive prophylactic treatment to alleviate or to delay eventual neuropathic response.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers both drugs.

Formulation of Pharmaceutical Compositions

The administration of each drug of the combination may be by any suitable means that results in a concentration of the drug that, combined with the other component, is able to correct the effect of elevated expression of PMP22 upon reaching the peripheral nerves.

While it is possible for the active ingredients of the combination to be administered as the pure chemical, it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and is may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastrointestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and anti adhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

The two drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate).

In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The emulsifying agents may be naturally occurring gums (e.g., gum acacia or gum tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. In a preferred embodiment, the drugs are formulated together, in the same excipient or carrier. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of two or more drugs that are subjects of this invention can be used together for the preparation of a medicament useful for reducing the effect of increased expression of PMP22 gene, preventing or reducing the risk of developing CMT1A disease, halting or slowing the progression of CMT1A disease once it has become clinically manifest, and preventing or reducing the risk of a first or subsequent occurrence of an neuropathic event.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration will be indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in the combination preferred for a unit dosage will depend upon several factors including the administration method, the body weight and the age of the patient, the severity of the neuropathic damage caused by CMT1A disease or risk of potential side effects considering the general health status of the person to be treated.

Additionally, pharmacogenomic (the effect of genotype on the pharmacokinetic, pharmacodynamic or efficacy profile of a therapeutic) information about a particular patient may affect the dosage used.

Except when responding to especially impairing CMT disease cases when higher dosages may be required, or when treating children when lower dosages should be chosen, the preferred dosage of each drug in the combination will usually lie within the range of doses not above the usually prescribed for long-term maintenance treatment or proven to be safe in the large phase 3 clinical studies.

For example,
for methimazole from about 0.5 to about 15 mg per day if taken orally. The special doses should be chosen if administered topically.
for pilocarpine from about 0.1 to about 20 mg per day if day if taken orally.

The most preferred dosage will correspond to amounts from 1% up to 10% of those usually prescribed for long-term maintenance treatment.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

Therapeutic Schema, Dosages and Routes of Administration

Below, the dosages for drug combinations (that differ in administration routes) in humans are described.

Methimazole and Pilocarpine
1—Administered orally as a single pharmaceutical composition: methimazole from about 0.5 to about 15 mg and pilocarpine from about 0.1 to about 20 mg every day orally for several months, the most preferred dosages for both drugs in the composition ranging from 0.6 to 35 mg per unit (per day).
2—Administered concomitantly orally for several months: methimazole from about 0.1 to about 15 mg and pilocarpine from about 0.02 to about 20 mg every day orally for several months, the most preferred dosages for both drugs in the composition ranging from 1.02 to 35 mg per unit (per day).
3—Administered concomitantly for several months: methimazole from about 0.05 to about 15 mg and pilocarpine from about 0.01 to about 20 mg every day orally for several months, the most preferred dosages for both drugs in the composition ranging from 0.06 to 35 mg per unit (per day).

The dosages of this drug in any combination among those disclosed in the present invention may differ in the formulations proposed for treatment of men or women.

Additional aspects and advantages of the present invention will be disclosed in the following experimental section, which should be considered as illustrative only.

EXAMPLES

I. In Vitro Experiments

Commercialized Rat Primary Schwann Cells

Vials of rat Schwann cells (SC) primary culture (Sciencell # R1700) are defrosted and seeded at the density of 10,000 cells/cm2 in "Sciencell Schwann cell medium" (basal medium from Sciencell # R1701) in poly-L-lysine pre-coated 75 cm$^2$ flasks. The culture medium is composed of basal medium, 5% Fetal Bovine Serum (3H-Biomedical AB #1701-0025), 1% Schwann cell growth supplement (3H Biomedical AB #1701-1752), 1% Gentamicin (Sigma #G1397) and 10 µM of Forskolin (Sigma # F6886) to promote their proliferation.

After reaching confluency (4 to 10 days depending on cell batch), Schwann cells are purified by gentle agitation or by thy1.1 immunopanning that allow SC isolation from adherent fibroblasts, to produce cultures that are at least 95% pure. SC are then counted (Tryptan blue method) and seeded in poly-L-lysine pre-coated 75 cm$^2$ flask in the same SC medium. At confluency, cells are rinsed, trypsinized (trypsin-EDTA 1× diluted from Invitrogen #1540054), diluted in PBS without calcium and magnesium) counted and platted in 12 well-dishes (140 000 cells/well) in Sciencell Schwann cell medium with 5% of FBS, 1% of cell growth supplement (CGS), 40 µg/ml of gentamicin and 4 µM Forskolin.

Custom-Made Rat Primary Schwann Cells

Primary Schwann cell cultures (SC) are established from Sprague-Dawley newborn rats (between P0 and P2) sciatic nerves. All newborn rats are sacrificed and isolated in a Petri dish. Dissection is performed under sterile conditions.

The dorsal skin is removed from the hind paw and the lower torso. The sciatic nerve is isolated and transferred to a culture dish containing ice-cold Leibovitz (L15, Invitogen #11415) supplemented with 1% penicillin/streptomycin solution (50 UI/ml and 50 µg/ml, respectively; Invitrogen #15070) and 1% of bovine serum albumin (BSA, Sigma A6003). Both nerves per rats are transferred in a 15 ml tube containing ice-cold L15. The L15 medium is then removed and replaced by 2.4 ml of DMEM (Invitrogen #21969035) with 10 mg/ml of collagenase (Sigma #A6003). Nerves are incubated in this medium for 30 minutes at 37° C. The medium is then removed and both nerves are dissociated by trypsin (10% trypsin EDTA 10×, Invitrogen #15400054) diluted in PBS without calcium and magnesium (Invitrogen #2007-03) for 20 min at 37° C. The reaction is stopped by addition of DMEM containing DNase I grade II (0.1 mg/ml Roche diagnostic #104159) and foetal calf serum (FCS 10%, Invitrogen #10270). The cell suspension was triturated with a 10 ml pipette and passed through a filter in a 50 ml tube (Swinnex 13 mm filter units, Millipore, with 20 µm nylon-mesh filters, Fisher). The cell suspension is centrifuged at 350 g for 10 min at room temperature (RT) and the pellets are suspended in DMEM with 10% FCS and 1% penicillin/streptomycin. Cells are counted (Tryptan blue method) and seeded in Falcon 100 mm Primaria tissue culture plates at the density of $5 \cdot 10^5$ to $10^6$ cells/dish.

After one day of culture, the medium is changed with DMEM, 10% FCS, 1% penicillin/streptomycin and 10 µM of cytosine b-D-arabinofuranoside (Sigma #C1768). 48 hrs later, medium is eliminated and cells are washed three times with DMEM. The SC growth medium is then added, composed of DMEM, 10% FCS, 1% penicillin/streptomycin, 2 µM of Forskolin (Sigma #F6886), 10 µg/ml of bovine pituitary extract (PEX, Invitrogen #13028). The medium is replaced every 2-3 days.

After 8 days of culture (4 to 10 days depending on cell batches), Schwann cells reach confluency and the culture, containing a large amount of contaminating fibroblasts, is purified by the thy1.1 immunopanning method. After this purification, cells are suspended in growth medium at 10 000 cells/cm2 in poly-L-lysine pre-coated 75 cm$^2$ flasks. Once they reach confluency, cells are rinsed, trypsinized (trypsin-EDTA), counted and platted in 12 well-dishes (100 000 cells/well).

Drug Incubation:

After cells being plated in 12 well-dishes, the medium is replaced by a defined medium consisting in a mix of DMEM-F12 (Invitrogen #21331020) complemented by 1% of N2 supplement (Invitrogen #17502), 1% L-Glutamine (Invitrogen #25030024) 2.5% FBS (Sciencell #0025), 0.02 µg/ml of corticosterone (Sigma # C2505), 4 µM Forskolin and 50 µg/ml of gentamycin. Growth factors are not added to this medium, to promote SC differentiation.

24 hours later, the medium is replaced by a defined medium (DMEM-F12) complemented with 1% Insulin-Transferrin-Selenium-X (ITS, Invitrogen #51300), 16 µg/ml of Putrescine (Sigma # P5780), 0.02 µg/ml of corticosterone and 50 µg/ml of gentamicin. At this step, neither progesterone nor forskolin are present in the medium.

One day later, primary Schwann cells are stimulated by drugs during 24 hrs (3 wells/condition). The preparation of each compound is performed just prior to its addition to the cell culture medium.

Pilocarpine (SIGMA) was tested in primary Schwann cells at 10 µM to 10 nM concentration range, while methimazole (SIGMA) was tested at 10 µM, 1 µM, 100 nM and 10 nM.

Drugs are added to a defined medium composed of DMEM-F12, with 1% Insulin-Transferrin-Selenium-X (ITS, Invitrogen #51300), 16 µg/ml of Putrescine, 0.02 µg/ml of corticosterone, 10 nM Progesterone and 50 µg/ml of gentamicin. The absence of Forskolin before and during drug stimulation avoids adenylate cyclase saturation.

Cultured Schwannoma Cells

Rat schwannoma RT4-D6-P2T cell line (ATCC #CRL2468™) is defrosted in DMEM (ATCC #30-2002) and 10% FCS (invitrogen #10106). The cells are maintained at 37° C. in a humidified incubator, in an atmosphere of air (95%.)—CO2 (5%). At passage n°4, cells are dissociated by trypsinization (+1 ml of Trypsin-EDTA, 0.25%-0.53 mM; Invitrogen) 5 to 15 min at 37° C. The reaction is stopped by addition of DMEM containing 10% of foetal bovine serum (FBS). Wells are counted in a Neubauer cytometer using the trypan blue exclusion test (Sigma). The suspension is triturated with a 10 ml pipette and the cells are then centrifuged at 350×g for 10 min at room temperature. The pellet of dissociated cells is resuspended and seeded on the basis of 30 000 cells/ml in 12 well-plates. 48 hrs later, the medium is replaced by a medium without serum (DMEM). After 15 hrs, RT4-D6P2T wells are stimulated by drugs added to the cell culture medium at the chosen concentration. The preparation of each individual drug or drugs combination is performed just prior to its addition to the cell culture medium.

Quantitative Reverse Transcriptase Polymerase Chain Reaction (Q-RT-PCR)

Quantitative RT-PCR is used to compare the levels of PMP22 mRNA after drug stimulation, relative with housekeeping RPS9 mRNA in RT4-D6P2T cell line.

8 hrs after drug incubation, cells are rinsed with cold sterilized PBS, total RNAs from each cell sample are extracted and purified from SC using the Qiagen RNeasy micro kit (Qiagen #74004). Nucleic acids are quantified by Nanodrop spectrophotometer using 1 µl of RNA sample. The RNA integrity is determined through a BioAnalyzer (Agilent) apparatus.

RNAs are reverse-transcribed into cDNA according to standard protocol. cDNA templates for PCR amplification are synthesized from 100 ng of total RNA using SuperScript II reverse-transcriptase (Invitrogen #18064-014) for 60 min at 42° C. in the presence of oligo(dT), in a final volume of 20 µl.

cDNAs are subjected to PCR amplification using the "LightCycler® 480" system (Roche Molecular Systems Inc.) Each cDNA are diluted five times before being used for PCR amplification. 2 µl of this cDNAs enters the PCR reaction solution with 5 µl of Master mix kit (Roche #04-887301001) in a final volume of 10 µl. Preliminary experiments ensured that quantitation was done in the exponential phase of the amplification process for both sequences and that the reaction efficiency is similar between target and housekeeping genes.

Taqman chemistry was used to perform RT-Q-PCR analysis. PCR reaction is performed by amplification of rat PMP22 (NM 017037) by using 500 nM of each primers (F and R) and 200 nM of probe Taq1 from Sigma-Aldrich.

The following PCR conditions are used: Denaturation 5 min at 95° C. followed by 10 sec at 95° C., 40 sec at 60° C. and 10 sec at 72° C. and 1 min at 40° C. (Forty amplification cycles). The relative levels of PMP22 gene expression are measured following the Ct method comparing the quantity of products generated from the target gene PMP22 and the PMP22 expression analysis by flow cytometry (FACS) 8 hrs, 24 hrs and 48 hrs after drugs incubation, supernatants of primary rat Schwann cells are recovered, centrifuged and frozen. SC are detached with trypsin-EDTA. As soon as the majority of cells are in suspension, the trypsin is neutralised using DMEM with 10% FCS.

Supernatants with cells are recovered and centrifuged. The pellets of cells are transferred in micro tubes, washed in PBS once and fixed with a specific solution (AbCys #Reagent A BUF09B). 10 minutes later, cells are rinsed once with PBS and kept at 4° C.

Five days after cell fixation, all cell preparations with different incubation times are labelled using the following protocol.

Cells are centrifuged at 7000 rpm for 5 minutes and the pellets are suspended in a solution of permeabilization (AbCys #Reagent B BUF09B) and labelled with primary PMP22 antibody (Abcam #ab61220, 1/50) for 1 hr at room temperature. Cells are then centrifuged at 7000 rpm for 5 minutes and cell pellets are rinsed once in PBS. A secondary antibody is added, coupled to Alexa Fluor 488 (goat anti-rabbit IgG, Molecular Probes #A11008, 1/100), for one hour at room temperature. Cells are then centrifuged at 7000 rpm for 5 minutes and cell pellets are rinsed once in PBS. The labelling is increased adding a tertiary antibody coupled to Alexa Fluor 488 (chicken anti-goat IgG, Molecular Probes #A21467, 1/100) for one hour incubation, at room temperature. Cells are then rinsed once in PBS. Control without any antibody (unlabelled cells) is performed to determine the level of autofluorescence and adapted the sensitivity of the photomultiplicators. Control with both secondary and tertiary antibodies but without primary antibody, is performed to assess non specific binding of antibodies.

Data acquisition and analysis are performed with a FACS Array cytometer and FACS Array software (Becton Dickinson) on 5000 cells. Forward Scatter (FSC) correlated with cell volume (size) and Side Scatter (SSC) depending on inner complexity of cells (granularity) are analysed. For expression of PMP22, analysis is performed within the total cells and percent of positive cells is calculated. Positive cells are cells with fluorescence intensity higher than the control with secondary antibody.

In order to quantify the number of SC, cells in control medium are analysed using antibodies anti-S100 Protein.

Cells are prepared according to the following protocol: Schwann cells are stained with antibody anti-S100 Protein (Dako #S0311, 1/100) for 1 hr at room temperature. This antibody is labelled according to protocol described above for PMP22 immunostaining but without incubation with tertiary antibody.

Results

We observed that PMP22 mRNA levels (FIG. 1) are significantly decreased in primary Schwann cells, and that 1 µM dose of pilocarpine induces the most important PMP22 down-regulation. *: $p<0.05$; ***: $p<0.001$; significantly different from control (pairwise student t test). On the right, exposed 24 hrs to pilocarpine, PMP22 mRNA level of expression is significantly down-regulated in primary Schwann cells even at low doses (10 nM and 50 nM). Similarly, we observed that pilocarpine (l µM) significantly decreases PMP22 protein level of expression after 24 hrs of incubation, by 38% in primary Schwann cells. This effect is still significant after 48 hrs of incubation (−18%, $p<0.001$).

In another experiment drugs (listed in Table 1) are incubated with rat schwannoma cell line during 8 hrs and PMP22 mRNA expression level was quantified by RT-Q-PCR.

The inventors have observed (FIG. 2) that while Methimazole (0.1 nm) and Pilocarpine (0.001 nm), used as individual drugs, exert no significant activity on PMP22 mRNA level of expression, this last one is significantly decreased by their combination. The synergic activity of these two drugs is illustrated in FIG. 2. These data demonstrate that at chosen concentrations the combination of pilocarpine and methimazole is able to down regulate significantly the expression of PMP22 gene in cultured Schwannoma cells, while pilocarpine and methimazole that are active at higher concentrations in primary Schwann cells do not decrease the level of expression of this gene in this system.

II. Experiments In Vivo in CMT Animal Model

The inventors have tested compounds and combinations for therapeutic effect in CMT transgenic rat model, a hemizygous PMP22 transgenic rats bearing three additional copies of mouse PMP22 gene show signs of demyelination in peripheral and cranial nerves, (Sereda et al., 1996; Grandis et al., 2004). At the mRNA level, an average 1.6-fold overexpression of PMP22 in CMT rats correlates with the clinical phenotype. A putative threshold level of PMP22 overexpression at which the wild type gene turns into a disease gene represents an obvious "target" to reach by treatment aimed at reducing PMP22 gene expression.

This CMT rat model is a good approximation of human CMT1A disease from a clinical point of view. Adult CMT rats exhibit a slowing of motor nerve conduction velocity with values similar to those of CMT1A patients, i.e., less than 50%. After sciatic nerve stimulation, compound muscle action potentials show reduced amplitudes and desynchronization. The histological and electrophysiological changes precede the overt clinical signs of motor impairment (Sereda et al., 1996, 2003). Axonal loss, confirmed by histological pronounced muscle atrophy, matches the human CMT1A symptoms.

The CMT rats already served as a model for an experimental CMT1A therapy (Meyer zu Hörste et al. 2007). In this model of CMT1A disease, the overt and hidden signs of pathology (locomotor deficiency, particular alterations in electrophysiological and tissue characteristics and, finally, the level of PMP22 over-expression appear to be the closest to those found in CMT1A patients).

The inventors have tested the compounds and combinations for therapeutic effect in a rat model. The experimental groups are formed with young rats of both genders separately. The rats are assigned to the groups following randomization schedule based on the body weight. In some experiments the randomization is based on the performances of the rats in the bar test. Both genders are represented by separate control littermates groups that are numerically equal or bigger than the treatment groups.

The rats are treated chronically with drugs—force fed or injected by Alzet osmotic subcutaneous pump (DURECT Corporation Cupertino, Calif.), depending on each drug bioavailability during 3 or 6 weeks.

The animals are weighted twice a week in order to adjust the doses to growing body weight. If the osmotic pump is chosen for the treatment administration, the doses of the drug are calculated on the basis of the estimated mean body weight of the animals expected for their age over the period of the pump duration (6 weeks). The pumps are re-implanted if necessary, with the appropriated anaesthesia protocol.

Behavioural Tests

Each three or four weeks the animals are subjected to a behavioural test. Each test is conducted by the same investigator in the same room and at the same time of the day; this homogeneity is maintained throughout entire experiment. All treatments and genotype determination are blinded for the investigator. "Bar test" and "Grip strength" has been mainly used to access the performance throughout study. The schedule of the bar test may change as the animal growth (in order to avoid the bias due to the learning, for example).

The assay of the grip strength allows detection of subtle differences in the grip performance that seems to be composed of the muscle force, sensitivity status (for instance, painful tactile feelings may change measured values of the force), behavioural component ("motivation"). The values differ between fore and hind limbs and greatly depend on the age of the animals.

The grip strength test measures the strength with which an animal holds on to a grip with its forepaws or its hindpaws separately. A dynamometer is placed with a grip to measure the strength (Force Gauge FG-5000A). The rat is held by the experimenter in a way that it grasps the grip either with its forepaws or with its hind paws and pulls gently the rat backwards until it releases the grip. The force measured when the animal releases the grip is recorded.

Two successive trials measuring the forepaws and two successive trials measuring the hindpaws strength per animal are processed; only the maximum score (one for forepaws and one for hindpaws) is noticed (in N).

The Bar Test

The bar test evaluates rats' ability to hold on a fix rod. Pmp22 rats which display muscular weakness, exhibit a performance deficit in this test (Sereda et al, 1996). The rat is placed on its four paws on the middle of the rod (diameter: 2.5 cm; length: 50 cm; 30 cm above the table). Trials are performed consecutively; the number (5 or 10) and the duration (30 or 60 sec) of trials in our experiments have been depending on batches of the animals. This variability in the testing has been introduced in order to determine the schedule appropriated to the best detection of the motor deficiency in the CMT rats in the course of the experiments.

Performance indices are recorded on each session:

The number of trials needed to hold for 60 sec or 30 sec on the rod.

The mean time spent on the bar (i.e. the fall latency) in each trial and the average on the session. In the experimental procedures the session ends after the rat has stayed two times for a cut-off time, i.e. 30 or 60 s, on the bar. A performance of the cut-off time (30 s or 60 s) is assigned to trials not completed.

The number of falls.

General Health Assessment

Body weights, overt signs (coat appearance, body posture, tremor) of the animals are monitored throughout the experiment. The rating scale is used for recording: 0=normal, 1=abnormal.

The Gait

Each rat is observed in a novel rat cage (dimensions 55×33×18 cm) without litter for five minutes. The gait of rats is evaluated with 4 parameters:

Score 0: normal gait (fluid)

Score 1: abnormal gait (not fluid or the rat has a slight limp)

Score 2: moderate incapacity (the rat drags one's leg and is able to put it right and walk)

Score 3: serious incapacity (the rat drags its one's or both hindpaws but is unable to put it/them right).

Inclined Plane Test

The sliding apparatus had a 30×50 cm plexiglas plane that could be inclined at an angle of 0° (horizontal) to 60°. Each rat was initially placed on the 25°-angled inclined plane in the up-headed position (head-up orientation); two trials separated by 1 min are performed. 30 min later, the same experiment is realized on a 35°-angled inclined plane then on 40°-angled inclined plane. During this time the rat was returned to its cage. The plane is cleaned after each trial.

The performances of rats are evaluated by 4 different scores:

Score 0: no slide
Score 1: a little slide (one or two paws)
Score 2: a moderate slide (4 paws) but not until the end of the plane
Score 3: the rat is sliding until the very bottom of the plane.

Electrophysiology

When appropriate, the rats are subjected to electrophysiological evaluation: the sensitive nerve conduction velocity as well as latencies and potential amplitude are measured.

NCV measurement and potential acquisition (subcutaneous) were performed with the help of the chain composed of an amplificator (AM System 1700 and/or EMG-UTC), a stimulator (Havard apparatus 223) and a computer equipped with an acquisition card and a software for acquisition (SPATOL) and for the signal treatment (CALVISE).

Animals were anesthetized using ketamine/xalazine and maintained on the thermostated plate at 37° C. throughout the test (anaesthetics were supplemented as needed). Stimulating silver needle electrodes were inserted in the proximal part of the tail. The recording electrode was inserted subcutaneously through about 1 mm of skin in the distal part of the tail (4 and 6 cm from the stimulating electrode). Constant-current square-wave stimuli, 0.2 s in duration, were administered at a frequency of 0.3 per second. Responses, amplified 5.000-20.000, were visualized and collected on a computer based data acquisition system. Latencies were measured at each wave onset (defined as the first clearly identifiable deflection from the baseline). Peak to peak amplitudes of the largest deflections were calculated to determine maximum amplitude. For each recording, measurements were performed on the averaged responses to at least ten identical stimuli.

Sensory related conduction velocity (SNCV) was calculated by division of the distance between the stimulating cathodes by the difference between the correspondent latencies obtained from the two sites of stimulation.

Histological Measurements

Upon the final tests (treatments being continued until the last day), the rats were euthanized. Hind feet of wild-type and transgenic rats were dissected and fixed by immersion in formal 4% solution for 48 hrs, and transferred in a 10% formol solution for 2 additional days. After being rinsed 15 min in water, they were then processed for decalcification for 26 hrs (Labonord Décalcifiant rapide No. 3 #DC3_09128300).

Feet were then transversally sectioned in two pieces that are processed for osmium coloration.

Tissues are hung up above 1% osmium tetroxyde solution (VWR, Osmium VIII oxide 0.5 g #20551.076) for 24 hrs and then rinsed with demineralised water for 4 to 6 hrs. Tissues are then dehydrated in automate of embedding (VIP2000 Vertical, Bayer Diagnostics) and classically embedded in paraffin.

Tissue sections of 4 μm are dehydrated in successive xylene and alcohol baths and mounted (Pertex glue, #T/00811_MICROM) for further analysis.

Image Analysis

Sections from the 6 animals were carefully chosen to illustrate the same anatomical level (toe junction) and are analyzed under Olympus microscope coupled with Saisam microvision software (Archimed Pro® 1997-2000 by Microvision Instruments). Peripheral nerve is localized and analyzed as follows: circulary myelinated fibers are counted (in a bundle nerve at least 150 fibers/animal). Cylindraxe diameters corresponding to inner perimeters of myelinated fibers and outer perimeters of the same fibers are determined. Then, we compared the distribution of myelin thickness and axons diameter in wild type and transgenic animals.

Furthermore, we measure optical density of the same nerve section to determine whether the non myelinated fibers content (not visible on osmium sections and so not analyzed) is higher in transgenic animals (reflected by a global pale appearance of the nerve section).

Finally, all foot muscles, present on the same section than used for nerve analysis, are manually outlined to determine global muscle surface. We then calculated the ration "muscle content/section surface".

Sciatic nerves are excised and used for weighting as well as for molecular biology and/or biochemical essays. (RT-Q-PCR for PMP22 mRNA and Western blots for myelin proteins quantifications; Cayman's EIA kits—for biochemical markers such as arachidonic acid metabolites, HPLC quantification for steroids and amines, ELISA for CNTF, IL-6 etc.) performed according to generally used protocols and for analytical procedures (drug concentrations measures).

The hind limbs muscles (soleus) are sampled, weighted, snap-frozen and preserved at −80° C. until analysis (the same as for sciatic nerves).

Results

Methimazole (0.35 mg/kg daily dose) and pilocarpine (0.2 mg/kg daily dose) administered by forced feeding improve bar test performances throughout the treatment procedure (FIG. 3), while compound PXT25 (which is presented here only for the sake of comparison) hardly shows any improvement.

The motor performances were on average 3-fold less successful in different CMT TG rats treated with placebo compared with Wild type (WT) group. The treatment with methimazole and pilocarpine allowed improvement of the TG animals in this experiment, the effect becomes statistically significant as early as after 8 weeks of the force-feeding.

The data show that CMT rats treated with methimazole and pilocarpine at these relatively high doses became significantly more performing compared with the placebo group. The group treated with compound pilocarpine even recovered the level of performance which is no more significantly differs from that of the WT placebo group.

The SNAP measured on the distal portion of the tail was found to be significantly diminished in the TG placebo group that may reflect the important axonal loss which in turn is due to the demyelination. This electrophysiological parameter turns to be significantly improved upon the treatment with compound A, (FIG. 4) while SNAP for the transgenic rats treated with compound B is approaching the nominal 5% threshold for significance.

This observation allows us to suppose that the action of methimazole may prevent the axon loss, even if the myelination status of the peripheral nerves is not measurably improved. The effect of pilocarpine seems to be essentially the same, even if because of the intra-group variability the difference with the placebo group parameter failed to reach statistical significance. In CMT1A, (sensory nerve action potential (SNAP) amplitude was more reduced and SNAP duration more prolonged than in CMT2. The reduction of composed muscle action potential (CMAP) and SNAP amplitudes in CMT1A is probably a combined effect of demyelination and axonal dysfunction. (Bienfait et al., 2006).

At the end of the study morphometrical analysis has been performed. The measurement of the hindlimb tissues reveals that the sciatic nerves and soleus muscles are significantly reduced in the CMT female rats treated with placebo compared with the control WT rats. (FIG. 5)

These deficiencies appear to be completely corrected by compound A treatment: the absolute masses of the muscles and the nerves are even higher than in the control WT rats, while the entire body weight is rather diminished in the compound A group comparatively with the placebo group (data not shown). The effect of pilocarpine treatment on the hindlimb muscle and nerves appears to be smaller than that of methimazole.

The Mix1 (Table 1) at 50 times lower doses of methimazole (4 mkg/kg) and pilocarpine (7 mkg/kg) improves the gait score of female rats after 10 weeks of forced fed treatment as shown in FIG. 6. We observed a positive trend after 6 weeks of treatment.

The following figures illustrate the positive effect of the mix 2 (Table 1) containing pilocarpine (7 mkg/kg); methimazole (4 mkg/kg), miferpristone (40 mkg/kg), naltrexone (4 mkg/kg; baclofen (60 mkg/kg and sorbitol (2 mg/kg) on male rats in 3 different behavioural and electrophysiological tests.

The FIG. 7 reveals that the Mix2 at these doses decreases the raise of the excitability threshold, found in the CMT placebo rats, after a nerve caudal electrical stimulation.

The FIG. 8 shows the positive effect of the Mix2 on the males' performances on the bar test; after 4 weeks of treatment, the number of falls is decreased and the time spent on the rod is increased.

The figure illustrates the fact that the Mix2 improves also the gait performances of the male rats after 3 weeks of treatment; the percentage rats walking with a fluid gait is increased by 35% for the treated rats compared to CMT placebo rats.

Similar results are produced for other combinations and summary of results could be shown in Table 1.

III. In Vivo Effect in a Model of Toxic Neuropathy

The drug treatments or regimen are orally administered from the day before the first intraperitoneal injection of Oxaliplatin 3 mg/kg (D-1) until the day before the last testing day (D16). Animals belonging to the Oxaliplatin-treated group are dosed daily with distilled water (10 ml/kg). Animals are dosed with the tested treatment and distilled water daily during the morning whereas Oxaliplatin is administered on the afternoon.

During the testing days (i.e. D1, D4, D10), the treatment and distilled water are administered after the test. Regarding the testing day (D4), including compounds and vehicle administrations and Oxaliplatin injection, the treatment and distilled water are administered prior to the injection of Oxaliplatin after the test. Animals from the reference-treated group are dosed only during the testing days (i.e. D1, D4, D10 and D17).

Cold allodynia is assessed by measuring the responses to thermal non-nociceptive stimulation (acetone test) on D1 (around 24 h after the first injection of Oxaliplatin 3 mg/kg (acute effect of Oxaliplatin), on D4, D10 and (chronic effect of Oxaliplatin) and on D17 (residual effect of Oxaliplatin one week after completion of treatment).

Testing is done using the acetone test 2 h post-administration of the reference.

The reference substance is Gabapentin, 100 mg/kg, per os (once a day×4 testing days).

Acetone Test

Cold allodynia is assessed using the acetone test. In this test, latency of hindpaw withdrawal is measured after application of a drop of acetone to the plantar surface of both hindpaws (reaction time) and the intensity of the response is scored (cold score).

TABLE 1

POS: reversion of disease symptoms in vivo

| effect in vivo combination | POS mix1 | POS mix2 | POS mix3 | POS mix4 | POS mix5 | POS mix6 | POS mix7 | POS mix8 | POS mix9 | POS mix10 |
|---|---|---|---|---|---|---|---|---|---|---|
| mifepristone |  | * | * | * | * | * | * |  |  |  |
| pilocarpine | * | * | * | * | * | * | * | * | * | * |
| methimazole | * | * | * | * | * | * | * | * |  | * |
| sorbitol |  | * | * | * | * | * | * |  |  |  |
| naltrexone |  | * |  |  |  |  |  |  |  |  |
| baclofen |  | * |  | * |  |  |  |  | * |  |
| rapamycin |  |  |  |  | * |  |  |  |  |  |
| ketoprofen |  |  |  |  |  | * |  |  |  |  |
| flurbiprofen |  |  |  |  |  |  | * |  |  |  |
| cevimeline |  |  |  |  |  |  |  | * |  |  |
| propylthiouracil |  |  |  |  |  |  |  |  | * |  |

| effect in vivo combination | POS mix11 | POS mix12 | POS mix13 | POS mix14 | POS mix15 | POS mix16 | POS mix17 | POS mix18 |
|---|---|---|---|---|---|---|---|---|
| mifepristone | * |  |  |  |  |  | * | * |
| pilocarpine | * | * | * | * | * | * | * | * |
| methimazole | * | * | * | * | * | * | * | * |
| sorbitol |  | * |  |  |  |  | * | * |
| naltrexone |  |  | * |  |  |  |  | * |
| baclofen |  |  |  |  |  |  | * |  |
| rapamycin |  |  |  | * |  |  | * | * |
| ketoprofen |  |  |  |  | * |  |  |  |
| flurbiprofen |  |  |  |  |  | * |  |  |
| cevimeline |  |  |  |  |  |  |  |  |
| propylthiouracil |  |  |  |  |  |  |  |  |

These data show that, in vivo, the combinations and regimens of this invention could allow effective treatment of CMT.

Reaction time to the cooling effect of acetone is measured within 20 sec (cut-off) after acetone application. Responses to acetone are also graded to the following 4-point scale: 0

(no response); 1 (quick withdrawal, flick of the paw); 2 (prolonged withdrawal or marked flicking of the paw); 3 (repeated flicking of the paw with licking or biting).

Six trials by rat are performed. For each experimental group, the results are expressed as the cumulative cold score defined as the sum of the 6 scores for each rat together±SEM. The minimum score being 0 (no response to any of the 6 trials) and the maximum possible score being 18 (repeated flicking and licking or biting of paws on each of the six trials).

Gabapentin: Source: Zhejiang Chiral Medicine Chemicals, China

Oxaliplatin: Source: Sigma, France

Results

Results of testing of mix2 in oxaliplatine are shown on FIG. 10. It is evident that mix 2 protects animals from neuropathy induced by toxic drug treatment.

IV. In Vivo Effect in a Model of ALS

Animal Model

We have chosen the SOD1$^{G93A}$ rat model (generated by Howland D S et al, 2002) to mimic the Amyotrophic Lateral Sclerosis pathology. This model overexpresses the mutated SOD1 gene in spinal cord, many brain regions as well as peripheral tissues (Howland D S et al, 2002). The onset of the motor neuron disease of this model is about at 115 days (Howland D S et al, 2002); it appears as hind limb abnormal gait. In few days, the paralysis of hind limb arises.

Experimental Procedures

We obtained colonies by crossing breeder SOD1$^{G93A}$ rats with Sprague Dawley female rats. Heterozygous SOD1$^{G93A}$ rats were identified with polymerase chain reaction (PCR) of tail DNA with primers specific for hSOD1 (Howland D S et al, 2002). Animals were maintained in a room with controlled illumination (lights on 0500-1900 h) and temperature (23±1° C.), and given free access to food and water. All the animal procedures in the present study were carried out in accordance with the guidelines standards of animal care.

Body weight measurement was performed every week and behavioral tests began at an age of 60 days and continued until endpoint. The treatments were administered every day per oral or subcutaneous way from the age of 5 weeks.

Observation test: characterization of the general aspect

Each rat was observed in a novel rat cage (dimensions 55×33×18 cm) without litter for five minutes. 5 different parameters are recorded:

The Gait
score 0: normal gait (fluid)
score 1: abnormal gait (not fluid or the rat has a slight limp)
score 2: moderate incapacity (the rat drags one's leg and is able to put it right and walk)
score 3: serious incapacity (the rat drags its one's or both hind paws but is unable to put it/them right)

The Coat Aspect
score 0: clean and silky coat
score 1: piloerection or dirty coat The Tremor
score 0: no tremor
score 1: tremor The Body Position
score 0: normal
score 1: abnormal (flattened or arching its back)

The Hindpaws Position
score 0: normal
score 1: spread hindpaws

The motor score test: characterization of the motor deficit

This test evaluates the ability of rats to right themselves within 30 sec of being turned on either side (righting reflex) (Gale K. et al, 1985).

A non-parametrical scoring system was used following these criteria (Matsumoto A. et al, 2006; Thonhoff J R et al, 2007):

score 0: the rat is unable to right itself from either side within 30 sec;
score 1: the rat is unable to right itself from only one side within 30 sec;
score 2: the rat is able to right itself from both sides within 30 sec but is unable to stand in the cage; it is always dragging some parts of body;
score 3: the rat is able to right itself from both sides within 30 sec, is unable to stand in the cage but is not dragging some parts of body;
score 4: the rat is able to right itself from both sides within 30 sec, is able to stand in the cage but has visible functional deficits;
score 5: the rat is able to right itself from both sides within 30 sec, is able to stand in the cage and no visible functional deficits.

The end-point of disease is fixed at score 0; the rat is then euthanized.

Inclined plane test: characterization of the motor deficit

The sliding apparatus had a 30×50 cm plexiglas plane that could be inclined at an angle of 0° (horizontal) to 60°. Each rat was initially placed on the 25°-angled inclined plane in the up-headed position (head-up orientation); two trials separated by 1 min are performed. 30 min later, the same experiment is realized on a 35°-angled inclined plane then on 40°-angled inclined plane. During this time the rat was returned to its cage. The plane is cleaned after each trial.

The performances of rats are evaluated by 4 different scores:
score 0: no slide
score 1: a little slide (one or two paws)
score 2: a moderate slide (4 paws) but not until the end of the plane
score 3: the rat is sliding until the very bottom of the plane The wire mesh test: characterization of the motor ability in difficult situation A wire mesh was placed in contact with a box at the top (at an angle of 70°) and the edge of a table at the bottom (Thonhoff J R et al, 2007). Each rat was placed on the bottom of the wire mesh and motivated to ascend by placing their littermates in the box at the top. Each rat was trained once a week (3 trials).

The recorded parameter was the latency time to reach the top of the wire mesh.

The open field test: characterization of the locomotor activity

The locomotor activity was measured in a Plexiglas box (45×45×30 cm, Acti-Track by BIOSEB, Lyon, France) with 16 photo-cell beams following the two axes, 1 and 5 cm above the floor.

The spontaneous and exploratory activity of each rat was evaluated during 3 hours.

4 parameters are recorded (the total travelled distance, the number of rearings, the percentage of travelled distance and of time spent in the center of the openfield).

BIBLIOGRAPHY

Amici S A, Dunn W A Jr, Murphy A J, Adams N C, Gale N W, Valenzuela D M, Yancopoulos G D, Notterpek L. Peripheral myelin protein 22 is in complex with alpha6beta4 integrin, and its absence alters the Schwann cell basal lamina. J Neurosci. 2006; 26(4):1179-1189.

Amici S A, Dunn W A Jr, Notterpek L. Developmental abnormalities in the nerves of peripheral myelin protein 22-deficient mice. J Neur Res. 2007; 85(2):238-249.

Anger T, Klintworth N, Stumpf C, Daniel W G, Mende U, Garlichs C D. RGS protein specificity towards Gq- and Gi/o-mediated ERK 1/2 and Akt activation in vitro. J Biochem Mol Biol. 2007; 40(6):899-910.

Atanasoski S, Scherer S S, Nave K-A, Suter U. Proliferation of Schwann Cells and Regulation of Cyclin D1 Expression in an Animal Model of Charcot-Marie-Tooth Disease Type 1A. J Neurosci Res. 2002; 67(4):443-449.

Bassi S, et al., Encephalo myelitis with thyro toxicosis. J Neur. 1978; 218(4): 293-296.

Batty I H, Fleming I N, Downes C P. Muscarinic-receptor-mediated inhibition of insulin-like growth factor-1 receptor-stimulated phosphoinositide 3-kinase signalling in 1321N1 astrocytoma cells. Biochem J. 2004; 379(Pt 3):641-651.

Bienfait H M, Verhamme C, van Schaik I N, Koelman J H, de Visser B W, de Haan R J, Baas F, van Engelen B G, de Visser M. Comparison of CMT1A and CMT2: similarities and differences. J. Neurol. 2006 December; 253(12): 1572-80.

Brancolini C, Marzinotto S, Edomi P, Agostoni E, Fiorentini C, Müller H W, Schneider C. Rho-dependent regulation of cell spreading by the tetraspan membrane protein Gas3/PMP22. Mol. Biol. Cell. 1999; 10: 2441-2459.

Castellone M D, Teramoto H, Gutkind J S. Cyclooxygenase-2 and Colorectal Cancer Chemoprevention: The B-Catenin Connection. Cancer Res. 2006; 66(23): 11085-11088.

Chies R, Nobbio L, Edomi P, Schenone A, Schneider C, Brancolini C. Alterations in the Arf6-regulated plasma membrane endosomal recycling pathway in cells overexpressing the tetraspan protein Gas3/PMP22. J Cell Sci. 2003; 116(Pt 6): 987-999.

Cosgaya J. M., Chan J. R., Shooter E. M. 2002. The Neurotrophin Receptor p75NTR as a Positive Modulator of Myelination Science 298; 1245-1248.

Devaux J J, Scherer S S. Altered ion channels in an animal model of Charcot-Marie-Tooth disease type IA. J Neurosci. 2005; 25(6): 1470-1480.

D'Urso D, Ehrhardt P, Müller H W. PMP 22 and protein zero: a novel association in peripheral nervous system myelin. J Neurosci. 1999; 19(9):3396-3403.

Fortun J, Dunn W A Jr, Joy S, Li J, Notterpek L. Emerging role for autophagy in the removal of aggresomes in Schwann cells. J Neurosci. 2003; 23(33): 10672-10680.

Fortun J, Go J C, Li J, Amici S A, Dunn W A Jr, Notterpek L. Alterations in degradative pathways and protein aggregation in a neuropathy model based on PMP22 overexpression. Neurobiol Dis. 2006; 22(1):153-164.

Fortun J, Verrier J D, Go J C, Madorsky I, Dunn W A, Notterpek L. The formation of peripheral myelin protein 22 aggregates is hindered by the enhancement of autophagy and expression of cytoplasmic chaperones. Neur. Dis. 2007; 25(2): 252-265.

Keltner J. et al. Myotonic pupils in Charcot-Marie-Tooth disease. Archives of ophtalmogy, 1975; 93(11):1141-1148.

Khajavi M, Shiga K, Wiszniewski W, He F, Shaw C A, Yan J, Wensel T G, Snipes G J, Lupski J R. Oral curcumin mitigates the clinical and neuropathologic phenotype of the Trembler-J mouse: a potential therapy for inherited neuropathy. Am J Hum Genet. 2007; 81(3): 438-453.

King T D, Song L, Jope R S. AMP-activated protein kinase (AMPK) activating agents cause dephosphorylation of Akt and glycogen synthase kinase-3. Biochem Pharmacol. 2006; 71(11):1637-1647.

Lupski J R, Wise C A, Kuwano A, Pentao L, Parke J T, Glaze D G, Ledbetter D H, Greenberg F, Patel P I. Gene dosage is a mechanism for Charcot-Marie-Tooth disease type 1A. Nat Genet. 1992; 1(1): 29-33.

Ma W, Li B S, Zhang L, Pant H C. Signaling cascades implicated in muscarinic regulation of proliferation of neural stem and progenitor cells. Drug News Perspect. 2004; 17(4):258-266.

Meyer Zu Horste G., Nave K-A. Animal models of inherited neuropathies. Curr. Opin. Neurol. 2006; 19(5): 464-473.

Meyer zu Horste G, Prukop T, Liebetanz D, Mobius W, Nave K A, Sereda M W. Antiprogesterone therapy uncouples axonal loss from demyelination in a transgenic rat model of CMT1A neuropathy. Ann Neurol. 2007; 61 (1): 61-72.

Nave K A, Sereda M W, Ehrenreich H. Mechanisms of disease: inherited demyelinating neuropathies. Nat Clin Pract Neurol. 2007; 3(8): 453-464.

Niemann S, Sereda M W, Rossner M, Stewart H, Suter U, Meinck H M, Griffiths I. R., Nave K-A. The "CMT rat": peripheral neuropathy and dysmyelination caused by transgenic overexpression of PMP22. Ann. N.-Y. Acad. Sci. 1999; 883:254-261.

Notterpek L, Shooter E M, Snipes G J. Upregulation of the endosomal-lysosomal pathway in the trembler-J neuropathy. J Neurosci. 1997; 17(11): 4190-4200.

Ogata T, Iijima S, Hoshikawa S, Miura T, Yamamoto S, Oda H, Nakamura K, Tanaka S. Opposing extracellular signal-regulated kinase and Akt pathways control Schwann cell myelination. J Neurosci. 2004; 24(30):6724-6732.

Passage E, Norreel J C, Noack-Fraissignes P, Sanguedolce V, Pizant J, Thirion X, Robaglia-Schlupp A, Pellissier J F, Fontes M. Ascorbic acid treatment corrects the phenotype of a mouse model of CMT disease. Nature Med. 2004; 10(4): 396-401.

Perea J, Robertson A, Tolmachova T, Muddle J, King R H, Ponsford S, Thomas P K, Huxley C. Induced myelination and demyelination in a conditional mouse model of Charcot-Marie-Tooth disease type 1A. Hum Mol Genet. 2001; 10(10):1007-1018.

Rangaraju S., Madorsky I., Go Pileggi J., Kamal A., Notterpek L. 2008. Pharmacological induction of the heat shock response improves myelination in a neuropathic model Neurobiology of Disease 32; 105-115.

Roa B B, et al. Charcot-Marie-Tooth disease type 1A. Association with a spontaneous point mutation in the PMP22 gene. N Engl J Med. 1993; 329(2): 96-101.

Robaglia-Schlupp A, Pizant J, Norreel J C, Passage E, Saberan-Djoneidi D, Ansaldi J L, Vinay L, Figarella-Branger D, Levy N, Clarac F, Cau P, Pellissier J F, Fontes M. PMP22 overexpression causes dysmyelination in mice. Brain 2002; 125(Pt 10): 2213-2221.

Sancho S, Young P, Suter U. Regulation of Schwann cell proliferation and apoptosis in PMP22-deficient mice and mouse models of Charcot-Marie-Tooth disease type 1A. Brain 2001; 124(Pt 11): 2177-2187.

Sereda M. et al. A transgenic rat model of Charcot-Marie-Tooth disease. Neuron. 1996; 16(5):1049-60.

Sereda M W, Meyer zu Horste G, Suter U, et al. Therapeutic administration of progesterone antagonist in a model of Charcot-Marie-Tooth disease (CMT-1A). Nat Med 2003; 9: 1533-1537.

Sereda M W, Nave K A. Animal models of Charcot-Marie-Tooth disease type 1A (CMT1A). Neuromol Med 2006; 8: 205-215.

Suter U, Scherer S S. Disease mechanisms in inherited neuropathies. Nat. Rev. Neurosci. 2003; 4: 714-726.

Suter U, Welcher A A, Ozcelik T, Snipes G J, Kosaras B, Francke U, Billings-Gagliardi S, Sidman R L, Shooter E M. Trembler mouse carries a point mutation in a myelin gene. Nature. 1992; 356(6366): 241-244.

Tashiro H, Fukuda Y, Hoshino S, Furukawa M, Shintaku S, Ohdan H, Dohi K. Assessment of microchimerism following rat liver transplantation. Transplant Proc. 1996 June; 28(3): 1279-80

Thomas P K, Marques W Jr, Davis M B, Sweeney M G, King R H, Bradley J L, Muddle J R, Tyson J, Malcolm S, Harding A E. The phenotypic manifestations of chromosome 17p11.2 duplication. Brain 1997; 120 (Pt 3): 465-478.

Tobler A R, Liu N, Mueller L, Shooter E M. Differential aggregation of the Trembler and Trembler J mutants of peripheral myelin protein 22. PNAS USA. 2002; 99(1): 483-488.

Ulzheimer J C, Peles E, Levinson S R, Martini R. Altered expression of ion channel isoforms at the node of Ranvier in P0-deficient myelin mutants. Mol Cell Neurosci. 2004; 25(1): 83-94.

Vallat J M, Sindou P, Preux P M, Tabaraud F, Milor A M, Couratier P, LeGuern E, Brice A. Ultrastructural PMP22 expression in inherited demyelinating neuropathies Ann Neurol. 1996; 39(6): 813-817.

Zelman S J, Rapp N S, Zenser T V, Mattammal M B, Davis B B. Antithyroid drugs interact with renal medullary prostaglandin H synthase. J Lab Clin Med. 1984; 104(2): 185-192.

We claim:

1. A method of treating toxic neuropathy in a subject in need thereof comprising the administration to said subject of a combination product or composition comprising:
   a) pilocarpine or a salt thereof;
   b) methimazole or carbamizole or a salt thereof; and
   c) a pharmaceutically acceptable carrier or excipient.

2. The method of claim 1, wherein said combination product comprises:
   a) a salt of methimazole and a salt of pilocarpine;
   b) a salt of methimazole and pilocarpine;
   c) methimazole and pilocarpine;
   d) methimazole and a salt of pilocarpine;
   e) carbamizole and pilocarpine;
   f) carbamizole and a salt of pilocarpine;
   g) a salt of carbamizole and pilocarpine; or
   h) a salt of carbamizole and a salt of pilocarpine.

3. The method of claim 1, wherein said combination product or composition further comprises at least one additional active compound.

4. The method of claim 3, wherein said at least one additional active compound is selected from baclofen, mifepristone, sorbitol, naltrexone, rapamycin, ketoprofen or flurbiprofen, or salts thereof.

5. The method of claim 3, wherein said combination product or composition further comprises:
   a) baclofen;
   b) mifepristone;
   c) sorbitol;
   d) naltrexone;
   e) rapamycin;
   f) cevimeline;
   g) ketoprofen;
   h) flurbiprofen;
   i) mifepristone, sorbitol and baclofen;
   j) mifepristone, sorbitol and rapamycin;
   k) mifepristone, sorbitol and ketoprofen;
   l) mifepristone, sorbitol and flurbiprofen;
   m) mifepristone, sorbitol, baclofen, and naltrexone;
   n) mifepristone, sorbitol, baclofen and rapamycin; or
   o) mifepristone, sorbitol, naltrexone and rapamycin;
   or salts thereof.

6. The method of claim 5, wherein said combination product or composition further comprises baclofen, mifepristone, sorbitol, and naltrexone, or salts thereof.

7. The method of claim 1, wherein said subject is a human.

8. The method of claim 1, wherein said combination product or composition is administered orally.

9. The method of claim 1, wherein said combination product or composition is administered repeatedly.

* * * * *

UNITED STATES PATENT AND TRADEMARK OFFICE
CERTIFICATE OF CORRECTION

PATENT NO. : 9,597,297 B2  
APPLICATION NO. : 14/269783  
DATED : March 21, 2017  
INVENTOR(S) : Daniel Cohen et al.

Page 1 of 1

It is certified that error appears in the above-identified patent and that said Letters Patent is hereby corrected as shown below:

In the Specification

Column 17,
Line 58, "(NM 017037)" should read --(NM_017037)--.

Column 24,
Line 5, "(D-1)" should read --(D -1)--.

Signed and Sealed this
Nineteenth Day of September, 2017

Joseph Matal
*Performing the Functions and Duties of the
Under Secretary of Commerce for Intellectual Property and
Director of the United States Patent and Trademark Office*